US00RE43482E

(19) United States
(12) Reissued Patent
Mikol et al.

(10) Patent Number: US RE43,482 E
(45) Date of Reissued Patent: Jun. 19, 2012

(54) INTRAMEDULLARY ROD APPARATUS AND METHODS OF REPAIRING PROXIMAL HUMERUS FRACTURES

(75) Inventors: Edward John Mikol, Myrtle Beach, SC (US); Thomas John Chambers, Myrtle Beach, SC (US)

(73) Assignee: Nuvana Medical Innovations, LLC, Myrtle Beach, SC (US)

(21) Appl. No.: 12/100,102

(22) Filed: Apr. 9, 2008

Related U.S. Patent Documents

Reissue of:
(64) Patent No.: 5,776,194
Issued: Jul. 7, 1998
Appl. No.: 08/638,940
Filed: Apr. 25, 1996

(51) Int. Cl.
*A61F 2/40* (2006.01)
*A61B 17/72* (2006.01)

(52) U.S. Cl. ..... 623/22.42; 623/19.14; 623/23.27; 623/22.46; 606/62; 606/64

(58) Field of Classification Search .... 623/19.11–19.14, 623/22.42, 22.46, 23.18, 23.26, 23.27, 23.28
See application file for complete search history.

(56) References Cited

U.S. PATENT DOCUMENTS 2,765,787 A 10/1956 Pellet
3,744,488 A 7/1973 Cox
3,814,089 A * 6/1974 Deyerle ..... 606/98
3,843,975 A 10/1974 Tronzo
3,893,196 A * 7/1975 Hochman ..... 424/422
3,990,438 A * 11/1976 Pritchard ..... 606/311
4,030,143 A * 6/1977 Elloy et al. ..... 623/19.12
4,101,985 A 7/1978 Baumann et al.
4,475,545 A * 10/1984 Ender ..... 606/64
4,503,847 A * 3/1985 Mouradian ..... 606/64
4,605,416 A * 8/1986 Grobbelaar ..... 623/23.27
4,653,487 A 3/1987 Maale
4,858,602 A * 8/1989 Seidel et al. ..... 606/60
(Continued)

FOREIGN PATENT DOCUMENTS

DE 3244243 C2 11/1986
(Continued)

OTHER PUBLICATIONS

The Grosse & Kempf Intramedullary Nailing System Brochure, Nov. 1986. See pp. 1-7, particularly pp. 3 and 6, (16 pages total).

*Primary Examiner* — David H. Willse
(74) *Attorney, Agent, or Firm* — The H.T. Than Law Group

(57) ABSTRACT

A bone stabilizing apparatus includes a stem member and an extension member, the stem member having a distal end for insertion within the intramedullary canal of a human humerus and the proximal end connected to the extension member. The extension member has radially directed threaded holes either pre-formed or created after the bone stabilizing apparatus is installed into the humerus. The threaded holes allow fixation of stabilizing screws with suture posts, or a washer structure to grip the surface of the bone and/or surrounding ligaments or muscle. A prosthetic or the natural humeral head can be attached to the extension member. In a preferred embodiment a guide structure directs the drill and stabilizing screws radially through the central axis of the extension member.

20 Claims, 16 Drawing Sheets

U.S. PATENT DOCUMENTS

| | | | | | |
|---|---|---|---|---|---|
| 4,895,572 | A | * | 1/1990 | Chernoff | 623/23.27 |
| 4,919,670 | A | * | 4/1990 | Dale et al. | 623/19.14 |
| 4,976,740 | A | * | 12/1990 | Kleiner | 623/23.14 |
| 5,041,114 | A | * | 8/1991 | Chapman et al. | 606/62 |
| 5,066,296 | A | * | 11/1991 | Chapman et al. | 606/64 |
| 5,080,685 | A | * | 1/1992 | Bolesky et al. | 623/22.42 |
| 5,112,333 | A | * | 5/1992 | Fixel | 606/62 |
| 5,163,961 | A | * | 11/1992 | Harwin | 623/22.46 |
| 5,167,666 | A | | 12/1992 | Mattheck et al. | |
| 5,176,681 | A | * | 1/1993 | Lawes et al. | 606/64 |
| 5,201,733 | A | * | 4/1993 | Etheredge, III | 606/53 |
| 5,282,865 | A | * | 2/1994 | Dong | 623/19.14 |
| 5,312,406 | A | * | 5/1994 | Brumfield | 606/64 |
| 5,314,479 | A | * | 5/1994 | Rockwood et al. | 623/19.14 |
| 5,358,526 | A | * | 10/1994 | Tornier | 623/19.14 |
| 5,441,500 | A | * | 8/1995 | Seidel et al. | 606/67 |
| 5,458,654 | A | * | 10/1995 | Tepic | 623/23.27 |
| 5,462,563 | A | * | 10/1995 | Shearer et al. | 623/20.11 |
| 5,472,444 | A | | 12/1995 | Huebner et al. | |
| 5,480,402 | A | * | 1/1996 | Kim | 606/64 |
| 5,489,309 | A | * | 2/1996 | Lackey et al. | 623/19.14 |
| 5,507,817 | A | * | 4/1996 | Craig et al. | 623/20.11 |
| 5,507,818 | A | * | 4/1996 | McLaughlin | 623/23.42 |
| 5,507,819 | A | * | 4/1996 | Wolf | 623/19.11 |
| 5,549,682 | A | * | 8/1996 | Roy | 623/19.14 |
| 5,620,445 | A | * | 4/1997 | Brosnahan et al. | 606/63 |

FOREIGN PATENT DOCUMENTS

| | | | | | |
|---|---|---|---|---|---|
| EP | 0 329 854 | | * | 8/1989 | |
| EP | 329854 | | | 8/1989 | 623/19 |
| EP | 0 441 577 | A2 | * | 8/1991 | |
| EP | 0565812 | A1 | | 10/1993 | |
| EP | 0 579 563 | A1 | * | 1/1994 | |
| EP | 0 617 934 | | * | 10/1994 | |
| EP | 617934 | | | 10/1994 | 623/19 |
| EP | 0 706 782 | A2 | * | 4/1996 | |
| FR | 2 619 502 | | * | 2/1989 | |
| FR | 261950 | | | 2/1989 | 623/19 |
| GB | 2 290 478 | A | * | 1/1996 | |
| SU | 921553 | | * | 4/1982 | |

* cited by examiner

INTRAMEDULLARY ROD APPARATUS AND METHODS OF REPAIRING PROXIMAL HUMERUS FRACTURES

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to an apparatus and method for the fixation of proximal humerus fractures in which one or more bone pieces must be aligned with the major portion of the bone. In proximal humerus fractures, displacing forces such as muscle connections acting on the fragments of the fracture frequently cause bone fragments to separate and pull away from the main part of the humerus. In alternative embodiments, this invention provides an apparatus and methods for internal fixation of fractured humerus bones, nonunions, and primary and metastatic tumors, in each case providing anatomic alignment to reduce impingement and promote healing.

2.Description of the Related Art

The conventional methods and apparatuses for treating proximal humerus fractures have respective shortcomings relating to effective treatment of many of the numerous categories of fractures. These categories correspond to proximal humerus fractures having predictable patterns. Specifically, displaced proximal humerus fractures are classified according to the displacement of humerus segments. Various apparatus and methods appear in the related art for treating proximal fractures of the humerus, including plates, screws, sutures and rods, but none of these solve all of the problems relating to fixation of these fractures.

One major problem in treating humerus fractures is the difficulty of finding adequate bone stock to secure the related art internal fixation means. The related art methods of fixation are therefore frequently difficult and unsuccessful, leading to possible loss of fixation, loss of fracture reduction, nonunion or malunion. Further, in many cases these methods do not allow early motion. Early motion is beneficial for cartilage nutrition and to prevent intraarticular adhesions and shoulder stiffness.

Some related art methods of fixation employ sutures attached to the rotator cuff musculature. Such a means of fixation does not provide the ease, anatomic alignment, and stability of the present invention, thereby also possibly leading to loss of fracture reduction or fixation.

A first conventional device, such as is shown in U.S. Pat. No. 4,919,670 to Dale et al., includes a stem portion for insertion into the intramedullary canal of the humerus and a head portion to replace the head of the humerus. This type of device is ineffective, however; at assisting in the fixation of bone fragments such as the lesser or greater tuberosity, or when the head of the humerus is to be saved. For example, the modular humeral prosthesis is designed to replace the natural humerus head and is not designed for a situation wherein the proximal humerus is fractured but the head is still attached or can be salvaged.

Another related art device is shown in U.S. Pat. No. 5,066,296 to Chapman et al describes an intermedullary rod used in the treatment of bone fractures. The Chapman apparatus utilizes an elongated body member inserted into a bone cavity and a tab member attached to the body member by a separate screw. The tab member has a transverse clearance aperture created prior to the tab member's attachment to the body member. A screw passes through the pre-formed clearance aperture, threads into a bone mass and pulls the bone against the tab member. The screw threads do not engage the tab member. Further, locking tabs on the tab member engage recesses on the body member, thereby eliminating any opportunity to rotate the tab member to selectively position the tab member aperture. This restriction limits the flexibility of this related art because, frequently, the pre-installed aperture cannot be optimally positioned. Further, this Chapman apparatus is applicable to diaphyseal fractures, i.e., fractures of the main bone shaft, and not metaphyseal or epiphyseal fractures such as proximal humerus fractures Still another related art device is shown by U.S. Pat. No. 5,112,333 to Fixel and relates to fixation of femoral and tibial bone fractures. This type of intramedullary nail provides fixation of fractures of bone shafts, in which the intramedullary nail provides compressive force to the separated shaft portions. The Fixel intramedullary nail, however, is not addressed to, nor effective for, proximal humerus fractures, particularly the segmented proximal humerus fractures. The reason that Fixel, and similar, methods are not effective for such segmented fractures is that the intramedullary nail secures bone fragments using individual screws attached to bone and traversing through the nail to attach to bone as well. With segmented proximal humerus fractures, however, there is frequently little bone stock suitable for the screws to anchor to, and the bone that is available is frequently weak. Further, in one embodiment directed toward the fixation of distal femoral or tibial fractures, the Fixel method requires the individual screws to pass through the slotted tip of the nail, thereby limiting the possible directions of approach. This may serve for femoral and tibial fractures, but is unlikely to work for proximal humerus fractures with its accompanying complex anatomy and fracture patterns. The reason is that, for such complex anatomy and fractures, there is need for significant freedom in the placement of fixation screws to allow the surgeon to capture each of the individual fracture fragments and fixate them. The alternative means employed by the intramedullary nail to secure bone fragments involves a plate, and a plate is not appropriate for use in many proximal humerus fractures wherein the strength of surrounding soft tissue or musculature and not the bone itself is the best means available for stabilizing the fracture. Additionally, a plate is very prominent, and may cause impingement.

Another related art device is described, for example, within U.S. Pat. No. 5,201,733 to Etheredge, III, and relates to the fixation of a bone fracture in which fractured bone pieces are first positioned and held in place with preferably bioabsorble screws and pins. Metal reconstruction plates are then attached to the external surface of the bone with screws, clamps, or pins, without regard to the location of the underlying bioabsorbable screws and pins. This Etheredge and related methods therefore rely on the strength of the bone to hold the plate, and in many patients with proximal humerus fractures the bone quality is not adequate for such fixation, thereby incurring the risk of loss of fixation of the fracture. Further, this method is generally ineffective in a proximal humerus fracture wherein multiple bone fragments are separated from the humerus. This is because a straight plate is not appropriate on a rounded humerus fragment, such as a head. Therefore, this Etheredge and related plate methods are best applicable for diaphyseal fractures only, not the metaphysical and epiphyseal types such as those that occur with proximal humerus fractures.

Another shortcoming of plate methods is that the installation of a plate involves stripping of the soft tissues from the bone. This is necessary for the plate to lie flat on the bone. The stripping, however, inhibits subsequent blood supply to the fragments because the soft tissue attachments provide that blood supply. This blood supply reduction can retard healing of the bone. Therefore, any fixation applied to the superficial surface of the bone risks damage to the blood supply of the bone fragments.

SUMMARY OF THE INVENTION

It is therefore an object of this invention to overcome the above-identified problems in the related art, and to provide an apparatus and methods for precise and stable fixation of proximal humerus fractures to promote correct anatomic bone position with reduced chance of bone fixation failure or later impingement.

It is a further object of this invention to provide a method and apparatus for fixation of a proximal humerus fracture that allows motion of the humerus early in a patient's recovery.

Another object of this invention is to provide a method of stabilizing a proximal humerus fracture using inventive screw means to stabilize the fracture.

A further object of this invention is to provide an apparatus that can be adapted for use with all categories of proximal humerus fractures.

A still further object of this invention is to provide for optional replacement of the proximal humeral head.

Another object of this invention is to provide a method and apparatus for stabilizing and repairing intraosseous cavities, voids, or pathologic fractures from primary and metastatic tumors.

A still further object of this invention is to provide a method and apparatus to stabilize and treat non-union and malunion of fractures.

A further object of this invention is to provide an improved method and apparatus for fixture and repair of humeral shaft fractures.

The present invention is directed to an apparatus for and method of treating proximal humerus fractures, humeral shaft fractures, nonunions and malunions of the proximal humerus or humerus shaft, and cavities resulting from primary and metastatic tumors. This invention also allows for reattachment or replacement of the humeral head. The method allows for internal fixation of fractures of substantially all known patterns.

In a general embodiment, the intramedullary rod of the present invention comprises a stem member and an extension member. The apparatus may be a one-piece structure of one material, or may be either a permanent or removable assembly of a stem member and an extension member.

The stem member is elongated, substantially cylindrical, and incorporates a plurality of transverse passages, either preformed or fabricated at time of insertion. Each transverse passage extends transversely through the longitudinal axis of the stem portion and is shaped for receiving stabilizing screws or equivalent structures for securing the intramedullary rod to the humerus. The proximal end of the stem member for this illustrated embodiment is slightly angled, relative to the central longitudinal axis of the major portion of the stem. Alternatively, the extension and stem member can be collinear.

In a first embodiment the extension member connects to the proximal end of the stem member, by threads or equivalent attachment means.

The extension member is formed of a material suitable for being drilled and, if self-threading screws are not used, tapped. The extension member is described further below as substantially cylindrical, but it can have a square, rectangular, triangular, or other shape in cross-section. Stabilizing screws, generally self-threading, are removably screwed into the intramedullary rod to apply fixation force to the fractured bone or associated soft tissue, for the purpose of stabilizing the humerus fracture and allowing it to heal. The fixation force is exerted by the stabilizing screw head, preferably through a force-distributing member, such as, for example, a claw washer, or by sutures looped through securing members formed on the stabilizing screws. This invention thereby provides a novel method of distributing the fixation force over a larger area of surrounding bone and soft tissue.

Another embodiment includes structure for fixing the natural humerus head to the extension member at a proper angle.

Still another embodiment includes a prosthetic humerus head with structure for attaching the prosthetic to the extension member at a proper angle.

A still further method and apparatus includes passages formed in the extension member through which a biocomposable glue or cement is injected, thereby filling intraosseous cavities between the extension member and surrounding bone material.

A further embodiment includes fixation devices inserted into the extension member and secured by a filling type cement into cavities in the proximal humerus.

As a still further embodiment, the present inventive method includes the steps of inserting the stem portion of the intramedullary rod into the medullary canal of the humerus; attaching the extension member to the stem portion; drilling and, optionally, tapping passages into the extension member; affixing a screw into such passages to provide means of gripping and stabilizing the fractured bone and surrounding tissue to the intramedullary rod, thereby realigning the fractured ends into anatomic position.

A further method includes an adjustable screw alignment guide which is removably and temporarily attached to the extension member to provide a guide for accurate and on-center drilling of the extension member.

BRIEF DESCRIPTION OF THE DRAWINGS

FIG. [3] *3A* depicts a removable screw alignment guide, shown inserted in the extension member.

DETAILED DESCRIPTION OF THE PREFERRED EMBODIMENTS

The structure and method of the present invention is described in the context of treating proximal fractures of the humerus. The present invention is, however, not limited to treating proximal humerus fractures, but may be used for treating other fractures of the humerus as well as fractures of other bones. It may also be used to treat nonunions, malunions, bone tumors, and cavitary lesions.

Figure 1:
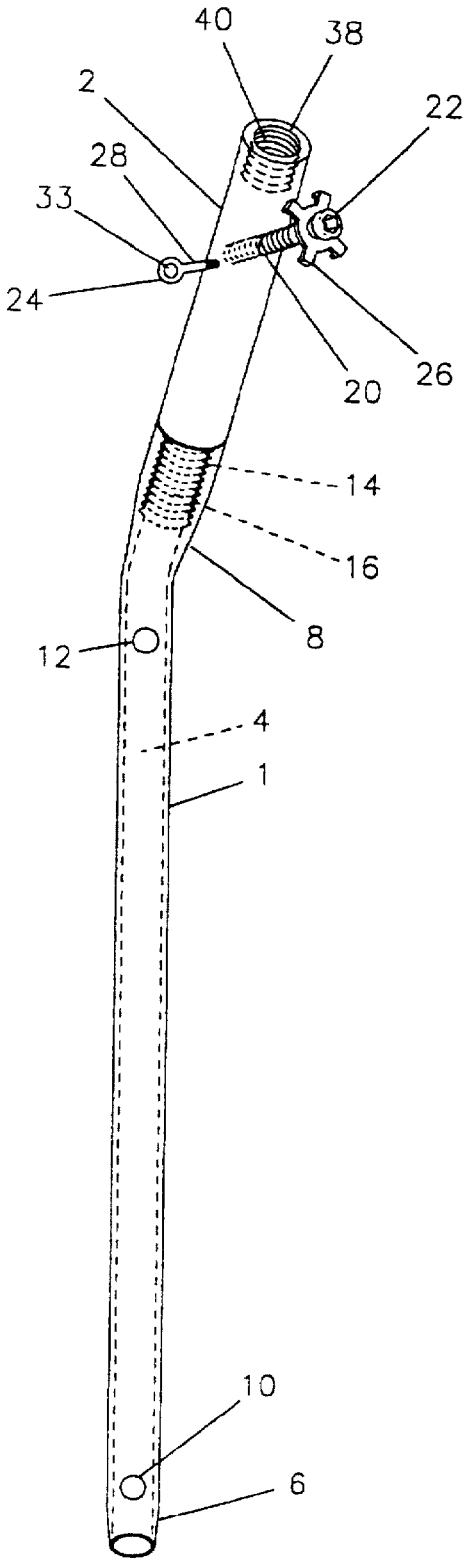
FIG. 1 depicts a lateral view of an intermedullary rod according to a first embodiment, with pressure-type and suture-type stabilizing screws shown inserted in the extension member.

The first embodiment of the present invention will be described in reference to FIGS. 1, 2A-2C, and 3. Referring to FIG. 1, this embodiment comprises a modular intramedullary rod having a stem member 1 and an extension member 2, forming a respective angle thereby allowing placement of the rod insertion site lateral to, i.e., not through, the articular surface. The stem member 1 is sized and shaped to conform to the basic humeral anatomy and in this embodiment is composed of metal, plastic (such as a high molecular weight polyethylene), composite, (such as polyethylene reinforced with carbon fibers or metallic filaments) or other suitable material. Extension member 2 is, in this embodiment, preferably solid, for both simplicity and strength, and is composed of plastic, composite (such as polyethylene reinforced with embedded carbon fiber or metallic filaments), or other suitable material that can be drilled and/or tapped. Preferably stem member 1, and extension member 2 will utilize a bioresorbable, possibly water insoluble, non-toxic material selected from the group of polymers consisting of polyglycolic acid, copolymers of glycolic acid and lactic acid, copolymers of lactic acid and aminocaproic acid, lactide polymers, homopolymers of lactic acid, polydesoxazon, polyhydroxybutric acid, copolymers of hydroxybutyric and hydroxyvaleric acid, polyesters of succinic acid and cross-linked hyaluronic acid, or other polymer.

Referring again to FIG. 1, stem member 1 is an elongated rod having a through-bore 4, and having a distal end 6 and proximal end 8. Respective to the distal and proximal ends are a distal transverse passage 10 and a proximal transverse passage 12. The passages 10 and 12 provide means for securing stem member 1 to the humerus at a point distal to the fracture site in proximal humerus fractures (10 and 12), or proximal (referring to passage 12) and distal (referring to 10) to the fracture site in humeral shaft fractures. The securing is accomplished by removably screwing interlocking screws (not shown) through passages 10 and 12. Although only one each of passage 10 and passage 12 are shown, it is understood by one skilled in the art that either or both distal 6 and proximal 8 ends may further incorporate a plurality of passages 10 and 12.

Passages 10 and 12 are preferably pre-formed when stem member 1 is composed of metal, but may be formed at any point along the stem member 1 at the time of the intramedullary rod's installation when stem member 1 is composed of plastic, composite, or other drillable and tappable material.

Through-bore 4 allows insertion of stem member 1 into the intramedullary channel of the humerus about a guidewire (not shown). Installation of the guidewire is well known in the art and shown, for example, in "Humeral Interlocking Nail System," an article in the booklet Surgical Technique by Russell-Taylor, incorporated herein by reference.

As shown in FIG. 1, proximal end 8 of stem member 1 is, in this embodiment, angled and, for this example, has internal threading 14 for attachment to the extension member 2 as described further below. Alternatively, the proximal end 8 of the stem member 1 could have an external threaded stud (not shown) fitting into a corresponding threaded hole (not shown) in the extension member 2.

Stem member 1 can be selected in length to extend any length down the intramedullary canal of the humerus. Extension member 2 has, for the depicted example of this embodiment, threads 16 on its distal end to fit the proximal end 14 of stem member 1. However, extension member 2 may be attached to stem member 1 by alternate means, such as a Morse taper pin (not shown) at the distal end 8 of extension member 2 and corresponding tapered hole (not shown) at the proximal end 8 of the stem member 1, or adhesive (not shown). Alternatively, one or more screws (not shown) could removably connect through both stem member 1 and extension member 2 after the distal end of extension member 2 is inserted into proximal end 8 of stem member 1. In another alternative means of attachment (not shown) extension member 2 is molded or otherwise attached, at its distal end to a metal adapter (not shown) which is threaded to removably attach to proximal end 8 of stem member 1. Further, stem member 1 and extension member 2 can be formed of a single unit, using material that is both drillable for extension member 2 and sufficiently strong for stem member 1.

The extension member 2 includes one or more substantially transverse passages 20 which are drilled, or otherwise created through extension member 2 at the time of fixation of the humerus fracture. Passages 20 are threaded and dimensioned so as to removably engage pressure-type or suture type stabilizing screws numbered as 22 and 24. The passages 20 are threaded, for example, by tapping or by using self-tapping screws for 22 and 24.

Figure 2B:
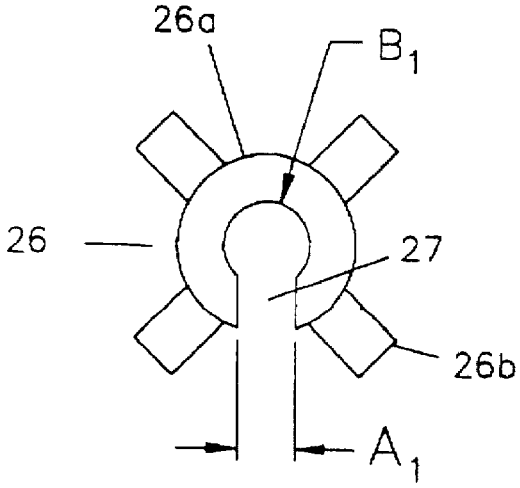
FIGS. 2A, 2B and 2C show details of the pressure screw, washer and suture mount of FIG. 1.
Figure 2C:
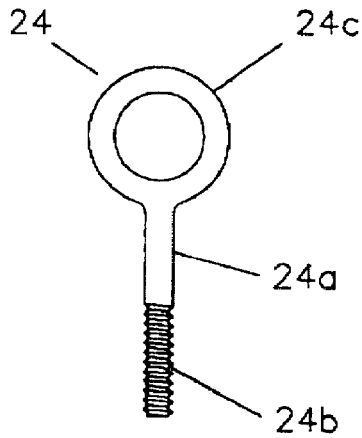
Figure 2A:
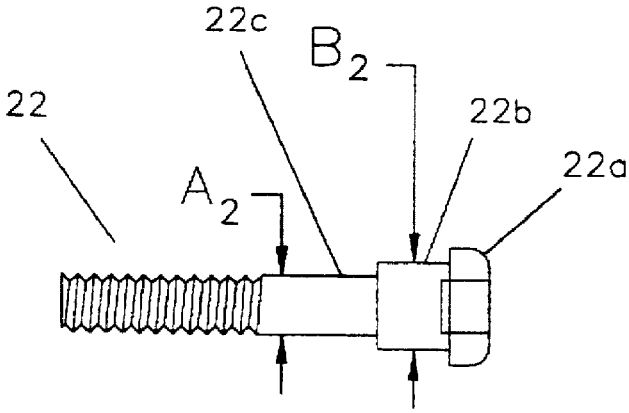

Pressure-type stabilizing screws 22, shown in detail in FIG. 2A, are preferably used in conjunction with a washer-like structure 26 to distribute the force of attachment over a wider area of bone and surrounding soft tissue than could be distributed by a screw alone. The washer 26 is preferably, as depicted in FIGS. 1 and 2B, a multiple-pronged claw washer having an area 26a for contacting the screw head 22a and a plurality of force-distributing claws 26b. Referring to FIG. 2B, the washer 26 is shown as having a slot 27 which, as described further below, permits it to be installed under the head 22a of screw 22 after the screw is started into the extension member 2 and is then locked into place as the screw 22 is tightened by the relative dimensions of the head 22a and the slot 27, as described further below. The washer 26 can be selected from various diameters and shapes according to the condition, size and shape of the proximal bone and tissue, and the nature of the fracture.

The suture-type stabilizing screw 24, shown in more detail in FIG. 2C, includes a shaft 24a, a threaded end 24b for secure, removable attachment to extension member 2, and an eyelet ring 24c at the opposite end, to which sutures may be fastened or through which sutures may be passed. The eyelet ring 24c has a substantially larger diameter than the shaft 24a in order to prevent an optional washer (not shown) from separating once installed at the fracture site.

In one alternative embodiment (not shown) extension member 2 is encased in a ribbed metal cover. In yet another embodiment (not shown) the extension member comprises a drillable plastic or bioabsorbable material having internal longitudinal wires or ribs (not shown) of metal or carbon fiber or other reinforcing material disposed within for added strength. The wires (not shown) would be suitably thin, so as not to interfere with drilling of the passages 20.

A person of ordinary skill in the art will appreciate that extension member 2 is envisioned in various dimensions as needed for particular applications.

Installation of the modular intermedullary rod preferably employs the screw alignment guide 34 shown in FIG. [3] *3A*. The screw alignment guide 34, as described below, attaches to the extension member via removable pivot pin 36, and adjusts along three axises for positioning, aligning, and centering passages 20 created in extension member 2. Pivot pin 36 is elongated and cylindrical, and removably connects to proximal end 38 of extension member 2 via, for example, threaded hollow channel 40. Alternate means for a removable securing of the pivot pin 36 to the extension member 2 are readily apparent to one of ordinary skill. For example, the pivot pin could slide into an equivalent of the threaded channel 40 and be secured by a lock screw (not shown) entering through a tapped hole (not shown) transverse to the extension member 2.

As shown in FIG. [3B] *3A*, screw alignment guide 34 thus rotates about the common axis of pivot pin 36 and extension member 2. The pivot pin 36 employs locking nut 42 to secure it to the extension member 2. The pivot pin 36 passes through the pivot hole 44 in the pivot arm 46 of the screw alignment guide 34, the pivot having sufficient clearance to allow linear motion of the pivot arm 46 along the axis A of the extension member and rotational motion around said axis B. Thumb screw 48, or an equivalent locking mechanism, reversibly locks the pivot arm 46 in a selected position.

Screw alignment guide 34 also includes an angle mechanism 50 for supporting at an adjustable angle, a guide holder 52. The guide holder 52 pivots about a pin 54, within plane C and allows adjustment of screw position within that plane while assuring intersection of the screw with the extension member. The angle mechanism 50 is locked in position by a thumb screw 56 or equivalent. The guide holder 52 holds, via a close fitting slip means, a drill sleeve 58. The guide holder 52 and drill sleeve 58 guide the drill bit (not shown) to ensure that the passage 20 is formed through the central axis A of extension member 2. The drill sleeve 58 is shown as a two-piece structure but a single piece sleeve (not shown) could be substituted.

It can be seen that screw alignment guide 34 allows for sufficient adjustment in orienting the guide holder 52 to allow passages to be quickly drilled, tapped, reamed, or otherwise created in any necessary orientation through extension member 2, regardless of visual obstruction from adjacent tissue and matter.

Figures 3A, 3B:
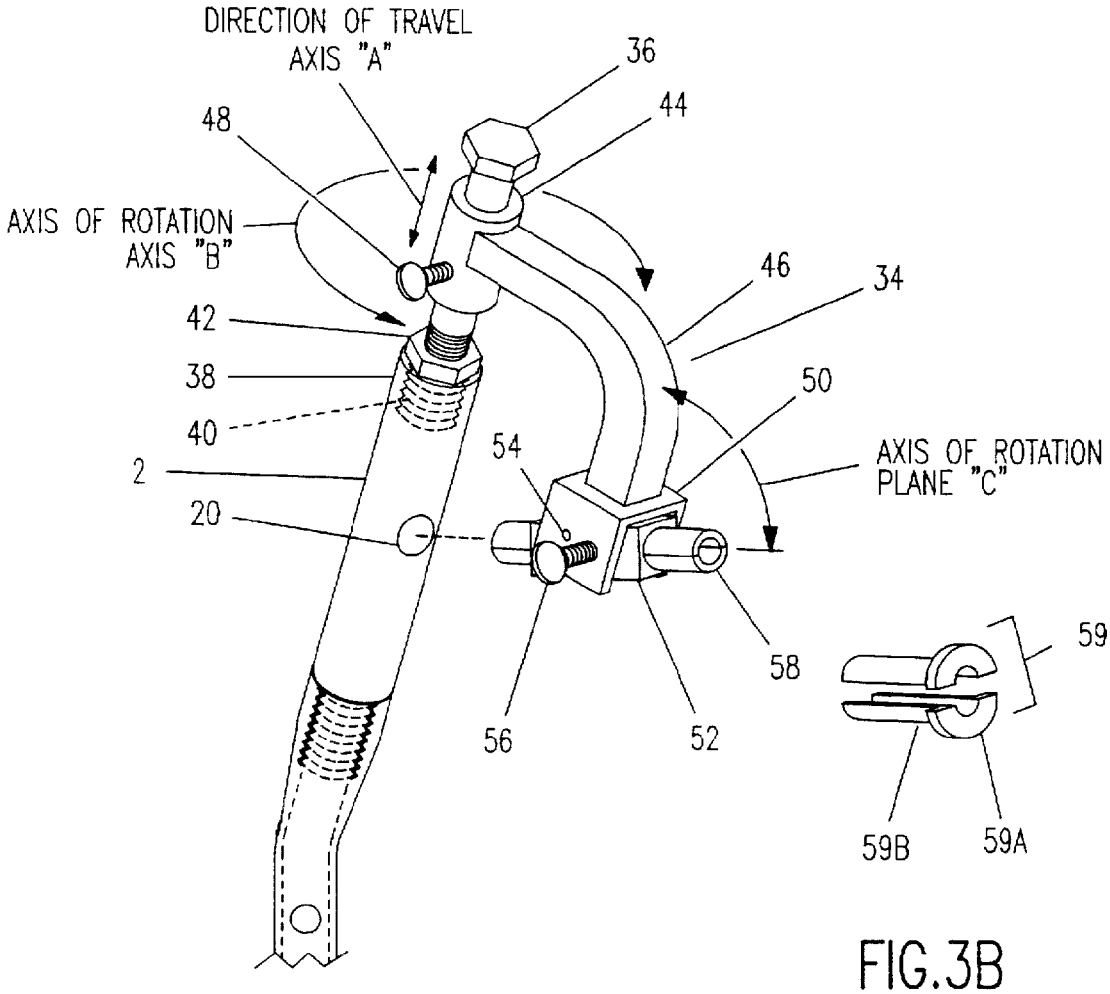
*FIG. 3B shows a screw guide sleeve usable with the screw alignment guide of FIG. 3A;*

Optionally, after the passages 20 have been formed the drill sleeve 58 is removed and, to better ensure proper orientation of stabilizing screws 22 and/or 24 to extension member 2, a screw guide sleeve 59 is inserted into the guide holder 52 in place of the drill sleeve 58. The screw guide sleeve 59 is a two-piece structure comprising a body 59a and a head 59b, *as shown in FIG. 3B*. The bore (not numbered) of the assembled and inserted sleeve 59 is slightly larger than the diameter of the screw head 22a shown in FIG. 2A and the outer dimension (not numbered) of the eyelet 24c of suture guide 24. This allows the screw guide sleeve 59 to be removed after the stabilizing screws 22 or 24 are started into the extension member 2.

One ordinarily skilled in the art will appreciate that use of this method and apparatus allows easy location of the target passage 20 for a stabilizing screw 22 or 24, even when passage 20 is not visible.

Figure 14B:
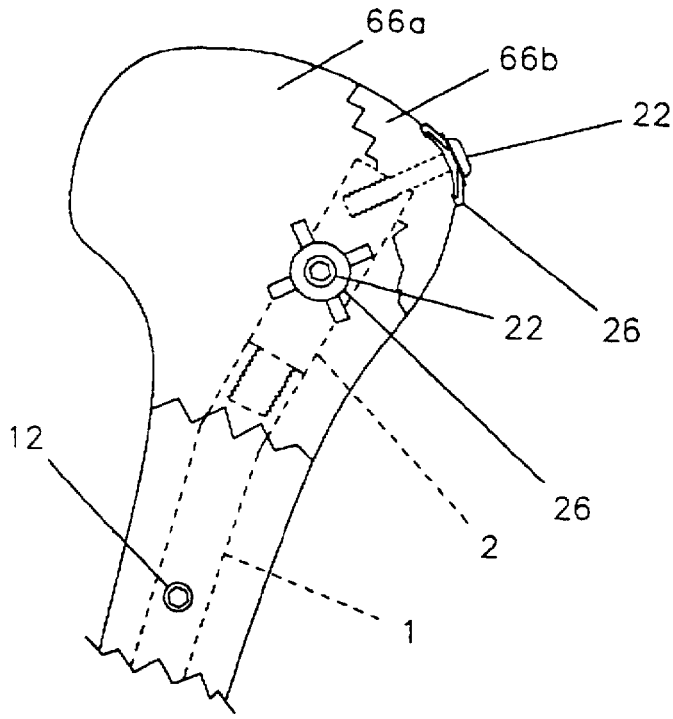
FIGS. 14A and 14B and are anterior directional views of the invention as applied to a three-part humeral fracture.
Figure 14A:
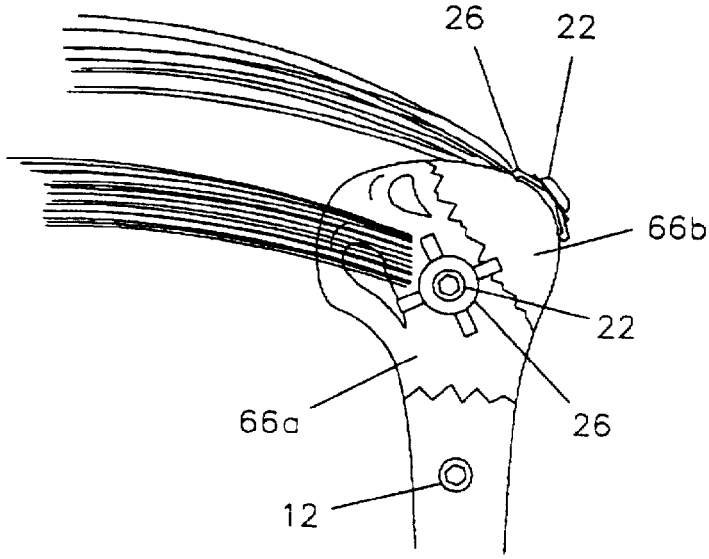

As described above, the present embodiment, as shown in FIG. 1, includes transverse passages 20 which are drilled, reamed, or otherwise created transversely through extension member 2 at the time of fixation of the humerus fracture. Passages 20 are threaded, such as, for example, by tapping, and dimensioned so as to removably engage pressure-type or suture type stabilizing screws numbered as 22 and 24. Alternatively, stabilizing screws 22 and 24 are of the self-tapping type, for which tapping would not be required. The number, placement, and angles of passages 20 depend upon the required fixation configuration, which is determined by the fracture pattern or other treatment concerns. Stabilizing screws 22 and 24 will, as necessary, pass first through the musculature, ligaments, or soft tissue attached to fracture fragments, then through the cortical bone of the fracture fragments, and anchor in the intramedullary rod, as shown in FIGS. 14A and 14B.

With reference to FIGS. 1, 2A and 2B, stabilizing screw 22 engages a multiple-pronged claw washer 26 that distributes the force of attachment over a wider area of bone and surrounding soft tissue than could be distributed by a screw alone. As shown in the FIG. 2B detail, the claw washer 26 includes a slot 27 having a width A1 slightly larger than the diameter A2 of the shaft 22c of pressure screw 22. The inner diameter B1 of the washer 26 is slightly greater than B2 to provide clearance for the shaft 22b of the screw 22, but smaller than the head 22a. The respective dimensions of slot 27, A1, A2, B1 and B2 permit the claw washer 26 to be inserted laterally under the screw head 22a after the screw 22 is started into the extension member 2. Further, since A1 is less than B2, the tightening of screw 22 causes B1 to engage B2, locking the washer 26 into place and preventing the washer from slipping out. The washer 26, for this example, has a plurality of relatively shallow prongs 26b extending outward, which grip soft tissue as well as bone. It will be understood by one skilled in the art that the prong pattern of claw washer 26 could be circular, or irregular, or rectangular. Further, prongs 26b may be perpendicular to the portion 26a of claw washer 26 as shown, or may extend from 26a at an angle (not shown). The ends of prongs 26b are preferably pointed, but this is not required to implement this invention. Prongs 26b may have a limited bending ability, thereby allowing one or more to be adjusted or removed as needed, depending on the fracture pattern.

Additionally, the juncture of prongs 26b to portion 26a of claw washer 26 may be curved. Further, the number of prongs 26b is not limited or restricted by the number illustrated in FIG. 1. Additionally, there may be multiple sizes to be used, depending on which fragment one is fixing and what its geometry is. For example, there may be a shape and form of a washer more useful for the lesser tuberosity and a differently shaped one for use with the greater tuberosity so each "kit" may have a variety of washers.

Alternatively, (not shown) a force-distributing washer (not shown) without prongs but having a suitably wide force distributing area could be used. However, by gripping surrounding bone and soft tissue, claw washer 26 allows fracture fragments to be correctly and anatomically aligned during fixation and held there firmly.

In addition, one of skill in the art may use this invention as shown in FIGS. 1, 14A and 14B by employing a screw as, for example, that shown as item 24, without a force distributing washer 26, if the bone is of sufficient strength.

Still further, one of skill in the art may use the slotted claw washer shown in FIG. 2B with a screw, such as 22, threaded directly into the bone instead of into the extension 2 of this embodiment. The dimensions of slot 27, i.e., having a width A1 slightly larger than the diameter A2 of the shaft 22c of the screw 22 and a diameter B1 greater than B2 of the shaft 22b, but smaller than 22a, permits the claw washer 26 to be inserted laterally under the screw head 22a after the screw 22 is started into bone material. This will obviate the problem of starting the screw, backing the screw out, placing the washer over the screw and then reinserting the screw, without incurring a problem of the washer slipping out via the slot 27.

It will be understood by one skilled in the art that the size and orientation of claw washer 26 and stabilizing screw 22 must be such as to avoid impingement with the acromion process, such that early and continued motion is possible after fixation of the fracture.

As described above, claw washer 26 and sutures (not numbered) threaded through the eyelet 24c of stabilizing screw 24 provide alternative methods of fracture fixation. Because stabilizing screws 22 and 24 are securely fastened to the extension member 2, it will be obvious to one skilled in the art that stabilizing screws 22 and 24 need not be affixed directly to bone, which is often a weak point for a fixture attachment. Of course, for additional stabilization, the length of screws 22 and 24 can be chosen to pass through the bone on one side of the extension member 2, thread through the extension member 2 and then pass back into the bone on the other side of the extension member 2.

Stabilizing screws 22 and 24 and claw washer 26 can be made of metal, plastic, composite, bioabsorbable (such as polyglycolic acid), or other suitable material. Further, claw washer 26 may be used with a pressure-type stabilizing screw 22, as shown in FIG. 1, or with a suture-type stabilizing screw 24 to provide additional pressure stabilization.

As a further embodiment of the present invention, after fixation of the humeral fracture, a threaded plug or cap (not shown) is threaded into the threaded hole 40 so as to cover the proximal end of extension member 2. The cap prevents bony and soft tissue ingrowth into the hole 40 of the extension member 2 and will facilitate later removal of the rod if needed.

Figure 4:
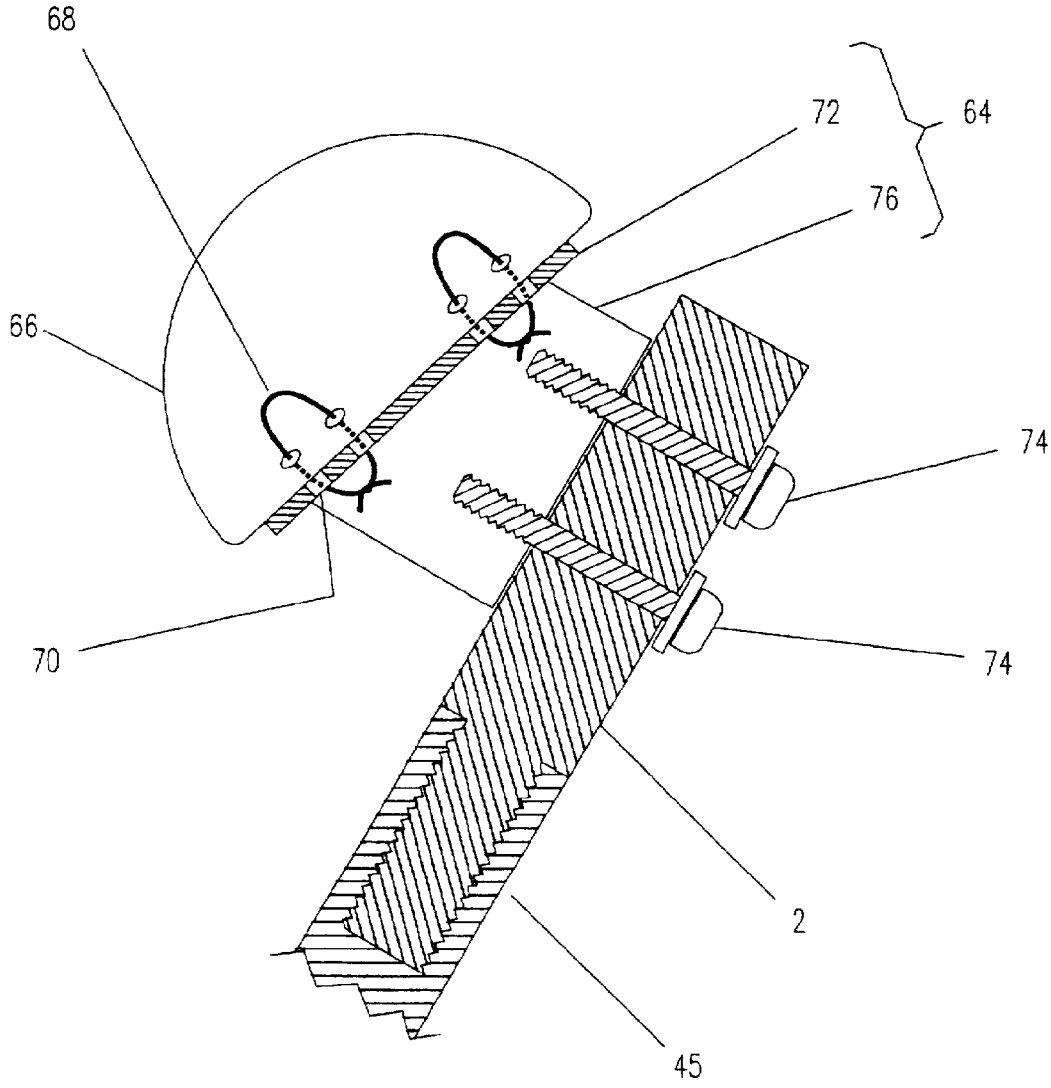
FIG. 4 is a partially cut-away lateral view of an angled fixation bracket attached to an extension member via screw means and to an anatomic head fragment via sutures.
Figure 5:
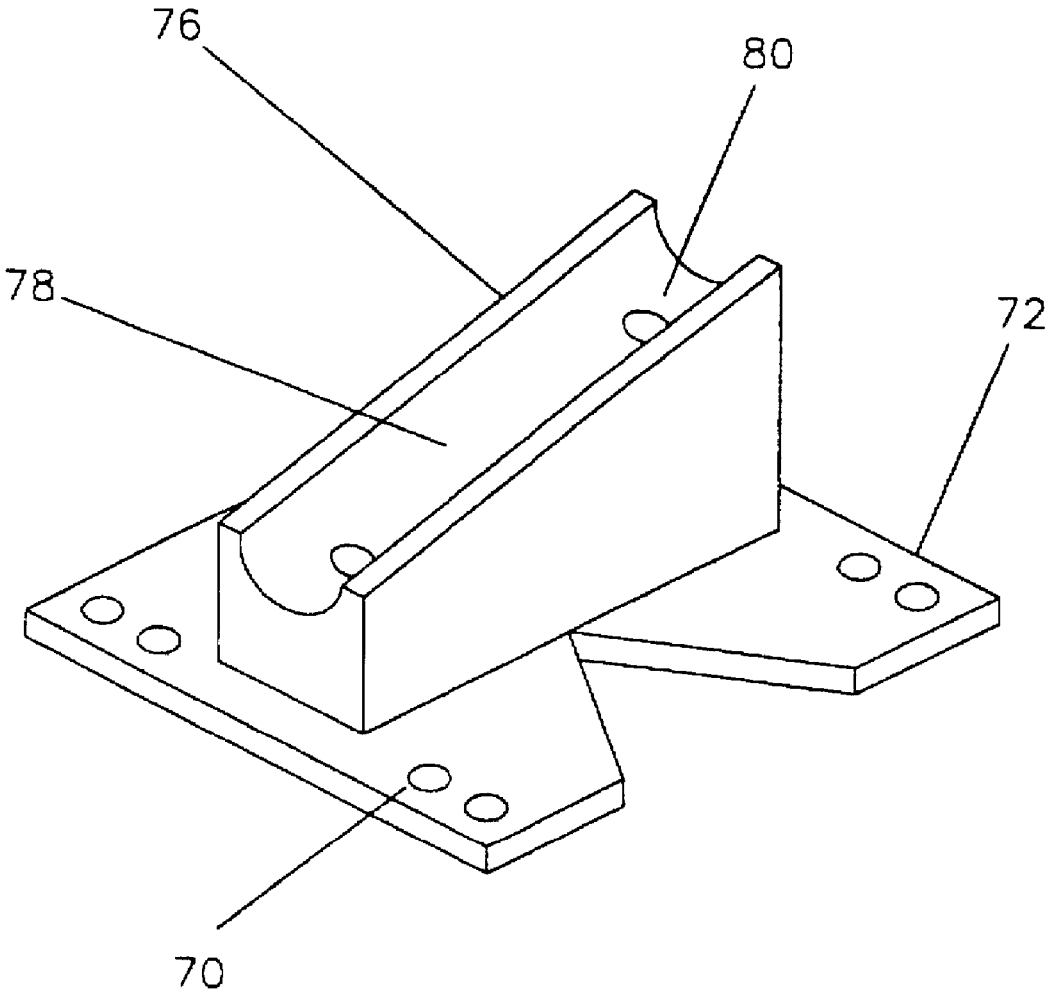
FIG. 5 shows a perspective view of the angled fixation bracket of FIG. 4.

Another embodiment, illustrated in FIGS. 4 and 5, permits ready fixation of anatomic neck fractures. This application obviates the need to employ an artificial prosthesis to replace the anatomic head of the humerus, as provided for in several versions of the related art. As shown in FIG. 4, this embodiment incorporates angled fixation bracket 64 to recreate the normal neck-shaft angle of the proximal humerus. Referring to FIGS. 4 and 5, in one embodiment, anatomic head fragment 66 is attached to angled fixation bracket 64 via sutures 68 that pass through pairs of holes 70 in the plate 72 of the angled fixation bracket 64 and into the humeral head. The angled fixation bracket 64 is mounted to the extension member 2 via bolts 74 passing through the extension member and into the mount block 76. The mount block 76 and the plate 72 can be an integral unit of a common material or an assembly of either like or dissimilar materials.

Preferably, angled fixation bracket 64 is composed of a bioresorbable, possibly water insoluble non-toxic, material selected from the group of polymers consisting of polyglycolic acid, copolymers of glycolic acid and lactic acid, copolymers of lactic acid and aminocaproic acid, lactide polymers, homopolymers of lactic acid, polydesoxazon, polyhydroxybutric acid, copolymers of hydroxybutyric and hydroxyvaleric acid, polyesters of succinic acid and cross-linked hyaluronic acid. However, other suitable materials include plastic, composite (such as polyethylene reinforced with carbon fibers or metallic filaments), or metal.

It will be understood by one skilled in the art that a small surface area for base plate 72 is preferred, to prevent obstruction of the healing ingrowth of bone.

As is best seen in FIG. 5, the mount block 76 has central, sloped, concave channel surface 78 formed to longitudinally fit extension member 2. Channel 78 may incorporate two or more pre-made apertures 80 for attaching angled fixation bracket 64 to extension member 2. Alternatively, apertures 80 are not pre-installed, therefore requiring drilling and possibly tapping at the time of installation. This drilling and optional tapping can be performed, if desired, with the screw alignment guide shown in FIG. 3A. Screws 74 are installed through extension member 2 and into the mount block 76, thereby removably securing angled fixation bracket 64 to extension member 2. Preferably, screws 74 are composed of a bioabsorbable material. Anatomic head fragment 66 is, preferably, first attached to angled fixation bracket 64, after which angled fixation bracket 64 is removably attached to extension member 2 of the intramedullary rod by screws 74. It can be seen that with the properly selected geometry of angled bracket 64, together the unlimited rotation for hole placement around axis B shown in FIG. 3, one can place the humeral head in the correct orientation to recreate the normal anatomy.

A variation (not shown) of the above embodiment uses an angle fixation bracket that is unitary, either made as a one piece unit or permanently attached, with the extension member 2. This would provide simpler structure with installation flexibility adequate for some instances.

Figure 6:
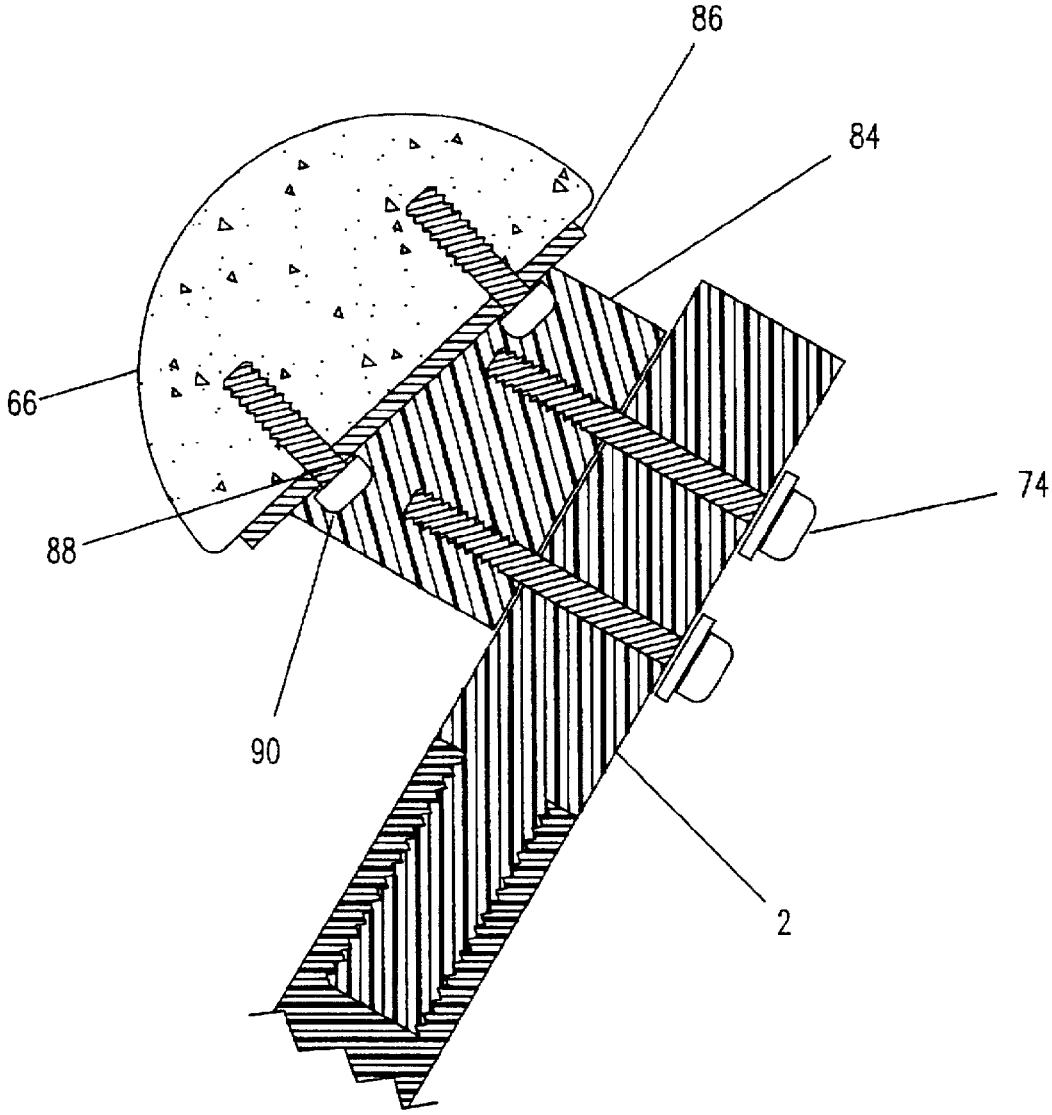
FIG. 6 is an alternate embodiment of FIG. 4, showing a lateral cutaway view of an angled fixation bracket attached to an extension member via screw means and to an anatomic humeral head via additional screw means.

In another embodiment, illustrated in lateral view in FIG. 6, an alternate angled fixation bracket 84 has a base plate 86 incorporating a plurality of clearance holes 88. Metal or bioabsorbable screws 90 pass through the clearance holes 88 and thread into the anatomic head fragment 66 to secure it to the angled fixation bracket 84.

Figure 7:
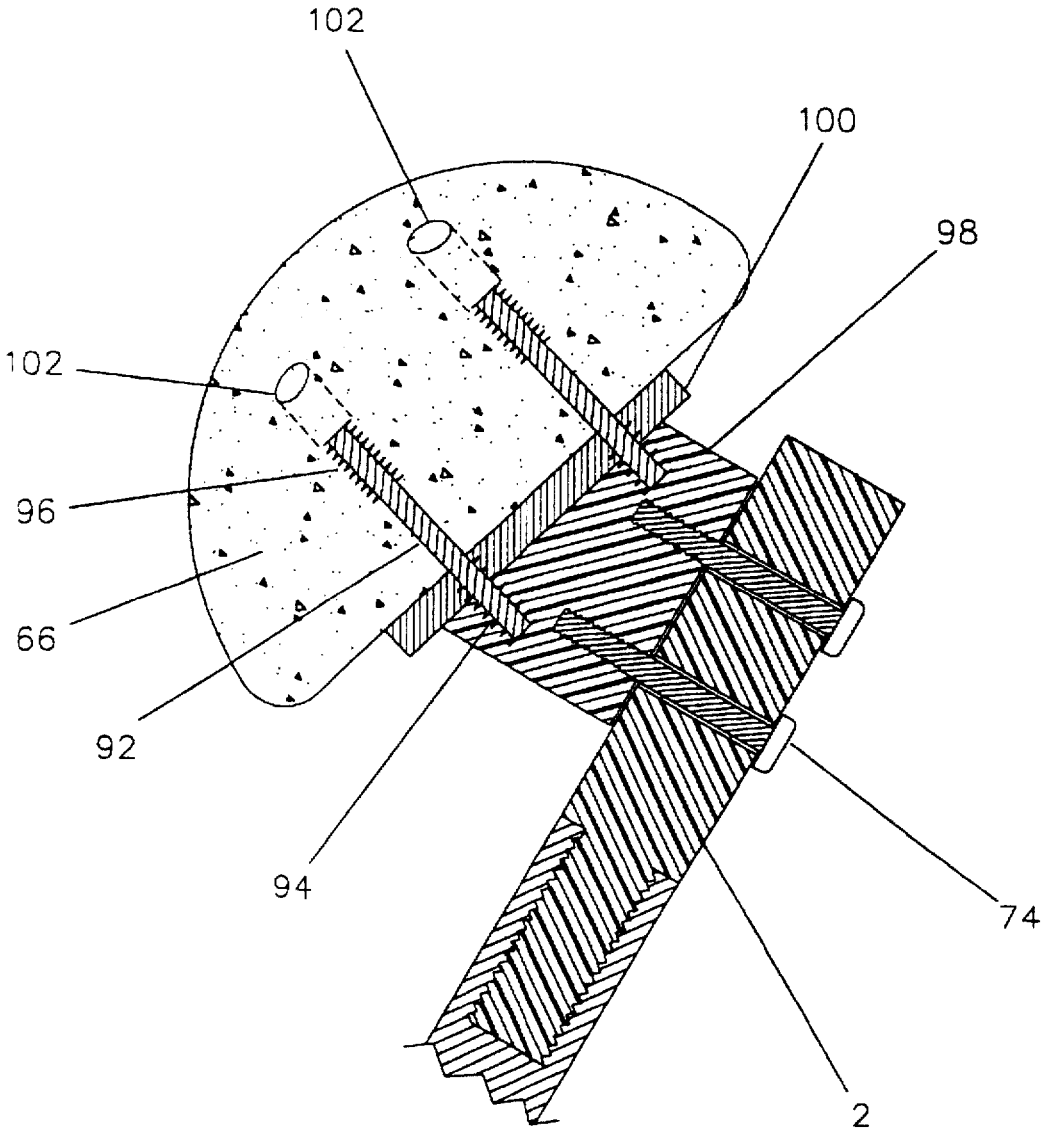
FIG. 7 is another alternate embodiment of FIG. 4. showing a lateral cutaway view of an angled fixation bracket attached to an extension member via screw means and to an anatomic humeral head via multiple-pitch "Herbert" screws.

In still another embodiment, shown in FIG. 7, "Herbert" type multiple pitch screws 92 are used. The "Herbert" screws 92, which may be made of a bioabsorbable material, have threads 94 of a first pitch and threads 96 of a second pitch. The pitch of the threads 94 is higher than the pitch of threads 96. The angled fixation bracket 98 of this embodiment is similar in shape to the fixation bracket 84 of the FIG. 6 embodiment. Securing of the anatomic head fragment 66 is accomplished because of the differing pitch of threads 94 and 96, causing threads 94 to advance into the head fragment 66 and then the angled fixation bracket 98 at a higher rate than threads 96 advance through the pilot holes 102 and into the head fragment 66. The anatomic fragment 66 is thus pulled against the plate 100.

Figure 8A:
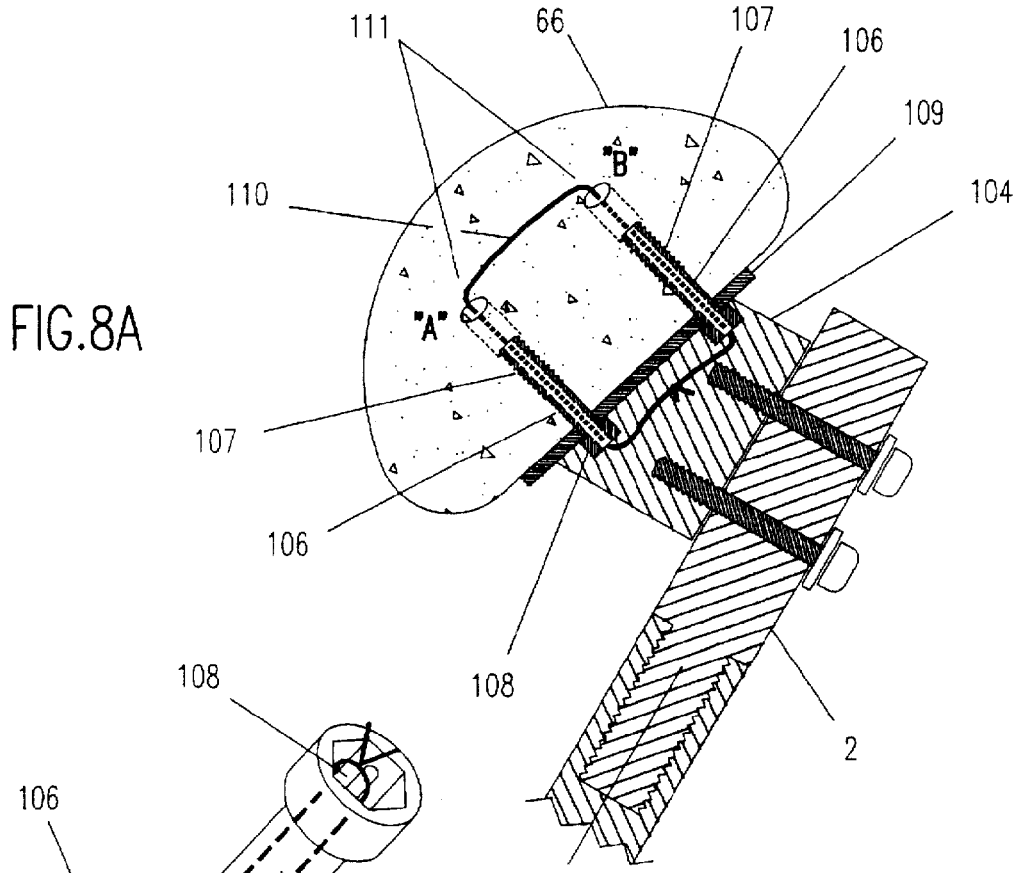
FIGS. 8A, 8B, and 8C show still another alternate embodiment of FIG. 4, showing a lateral view of an angled fixation bracket attached to an extension member via screw means, and to an anatomic humeral head via cannulated screws and associated sutures.
Figure 8C:
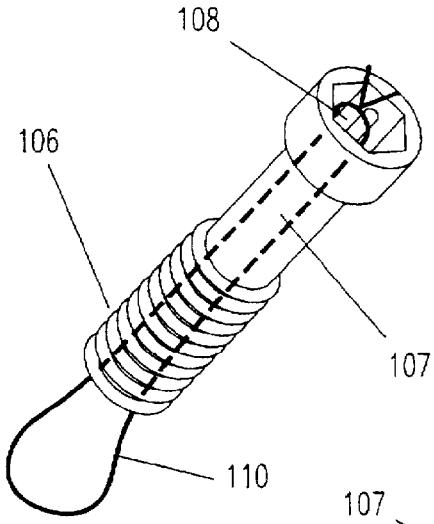
Figure 8B:
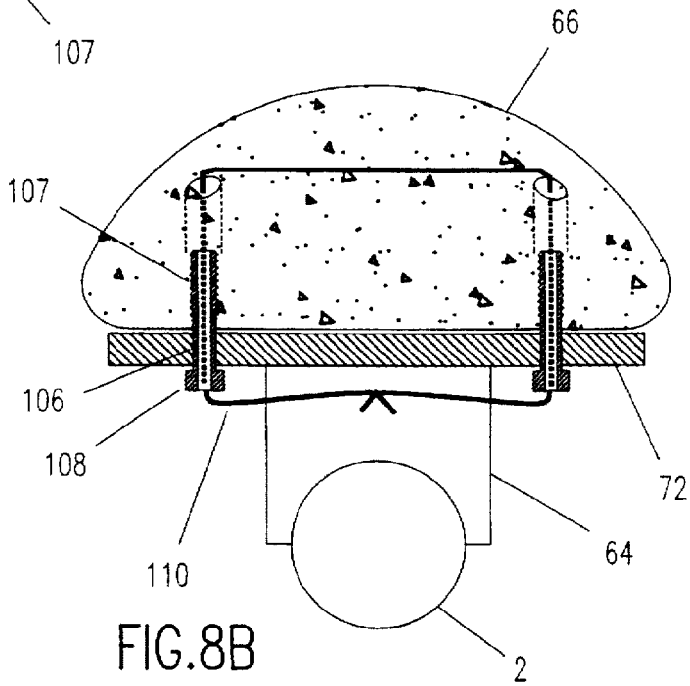

Still another embodiment, shown in FIGS. 8A, 8B and 8C, comprises an angled fixation bracket 104 having the same basic shape the fixation bracket 84 of FIG. 6, but using cannulated screws 106. The cannulated screws 106 have a hollow longitudinal channel 107, a suture bar 108 at one end and threads (not numbered) for engaging the bone on the other end. The cannulated screws 106 may be formed of a bioabsorbable material. As shown in FIGS. 8A and 8B, the cannulated screws 106 are used with sutures 110, which pass through channels 107, and through holes 111 drilled through the anatomic head 66. The sutures 110 can be tied in a knot 111a, as shown in FIGS. 8A and 8B, or tied around the bar 108 shown in FIG. 8C, or both, thereby attaching the anatomic head fragment 66 to the plate 109. Alternatively, the anatomic head fragment 66 can be attached by routing the suture 110 through the bore 107, through an exit hole (not shown) in the anatomic head 66, back through a return hole (not shown) in the head, back through the bore 107, and then tied around the bar 108, as shown in FIG. 8C. On the other hand, depending on the tie manner employed, the suture arrangement of FIGS. 8A and 8B may render the suture bars 108 unused and, optionally, cannulated screws without the bars (not shown) can be used.

Alternatively, instead of cannulated screws 106, hollow pegs (not shown), either with or without suture tie bars (not shown) could be pre-formed on or formed integral to, or pre-pressed into, or fixed on the angled fixation bracket plate 109, protruding at the location were clearance holes 88 or suture holes 70 are shown. Sutures would pass through these pegs (not shown) and allow ready attachment of the anatomic head fragment 66.

Attachment by sutures or bioabsorbable screws, as described above, facilitates later removal of the angled fixation bracket, and the entire intramedullary rod if necessary, such as during an arthroplasty if humeral head replacement becomes necessary later.

Figure 9:
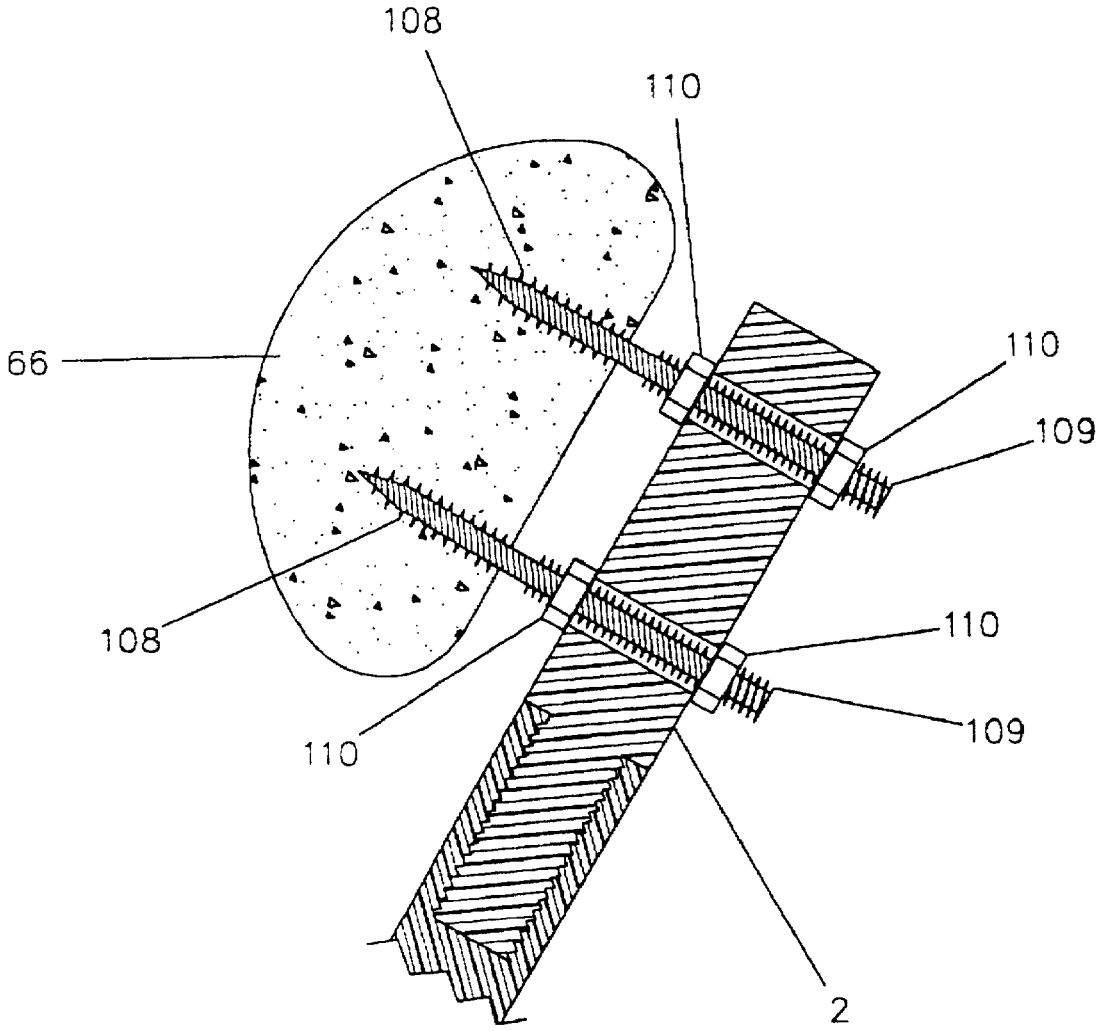
FIG. 9 depicts one embodiment of an apparatus for attaching an extension member to a separated neck fragment, with locking nuts to prevent collapse.

As shown at FIG. 9, it is envisioned that the present invention may also stabilize anatomic neck fractures by attaching screws 108 through clearance holes (not numbered) in extension member 2 and directly into anatomic head fragment 66. Screws 108 are prevented from slipping through extension member 2 by the use of locking nuts 110 which are respectively loosened and tightened to obtain the desired distance from the head to the extension member. The angle at which anatomic head fragment 66 is secured will thus reflect the normal neck-shaft angle. The threaded portion of screws 108 extending into the anatomic head fragment 66 is preferably self tapping and is not required to have the same thread pitch as the portion of 108 onto which lock nuts 110 engage.

Figure 10:
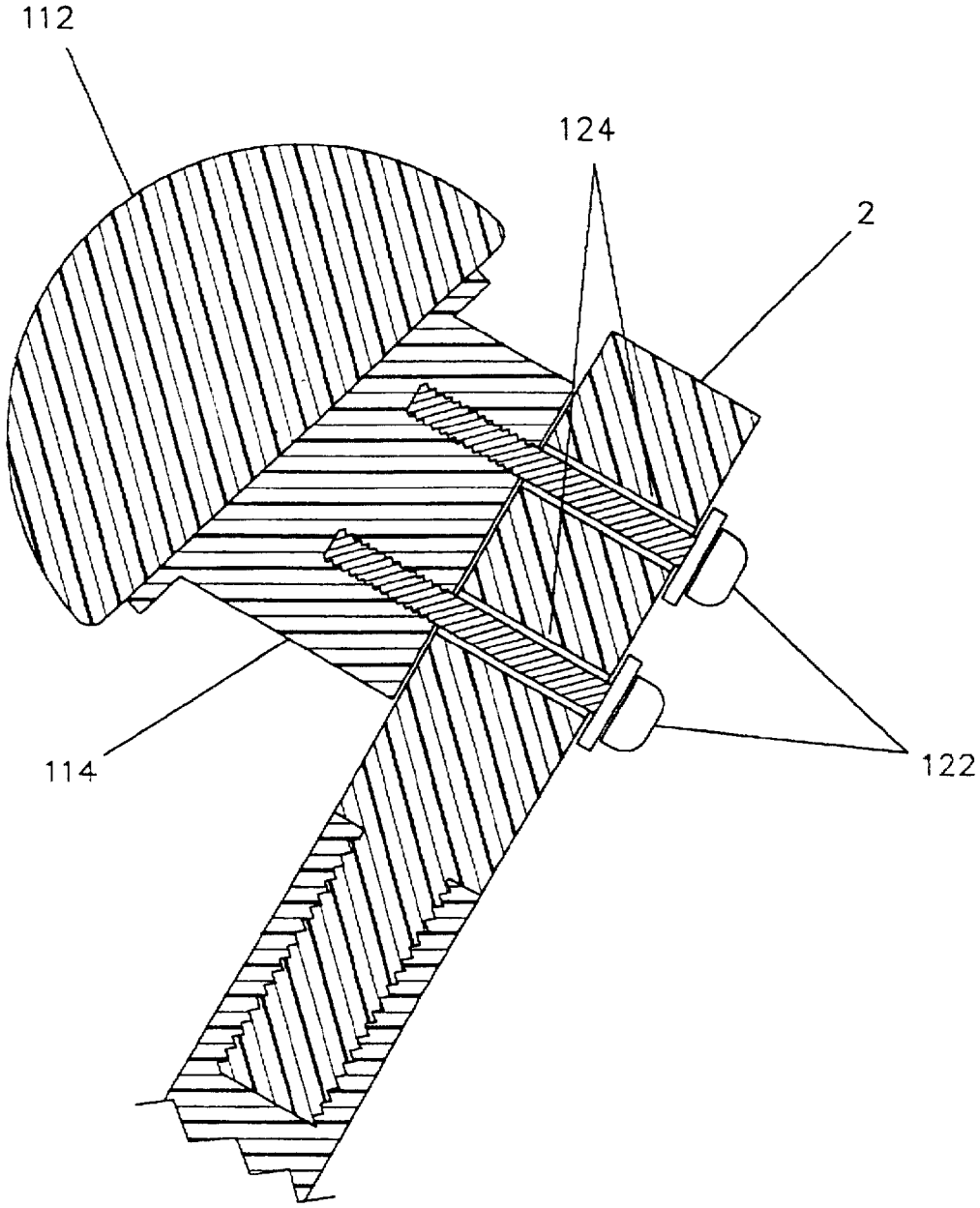
FIG. 10 depicts one embodiment of an apparatus for and method of attaching an extension member to an artificial prosthetic head/neck replacement of a head/neck fragment.

Referring to FIG. 10, it is also envisioned that when the anatomic head fragment of a proximal humerus fracture is unsalvageable, the fragment may be replaced with an artificial head prosthesis 112. Head prosthesis 112 is attached to extension member 2 with an angled spacing member 114, to securely mount the prosthesis 112 at the proper neck-shaft angle. As shown in FIG. 10, the head prosthesis 112 and angled spacing member 114 are unitary, either as a single piece or a permanent assembly. Alternatively (not shown) the head prosthesis 112 could be mounted by screws (not shown) to the angled spacing member 114. Referring to FIG. 10, the angled spacing member 114 is attached to the extension member 2 by screws 122 through clearance holes 124 formed, either at time of manufacture or at time of installation, in the longitudinal axis of extension member 2. Head prosthesis 112 may be composed entirely of metal or of a metallic articular surface with a plastic backing. As a further alternative, head prosthesis 112, angled spacing member 114 and the extension member 2 could be formed as a unitary member.

For the embodiments of FIGS. 6 and 8, a head alignment template guide (not shown) may be used to align and guide self-threading screws 108 and 90 to removably connect head fragment 66. Similarly. for the embodiment of FIG. 10, a head alignment template guide (not shown) may be used to drill and then align and guide self-threading screws (not shown) into the head prosthesis 112. Further a template-type head alignment guide would assist drilling holes into head fragment 66 to match the angle fixation bracket of the embodiments of FIGS. 4 and 5 as well. Alternatively the base plate of the angled fixation bracket of these FIG. 3-9 embodiments may be predrilled as a guide.

Figure 11:
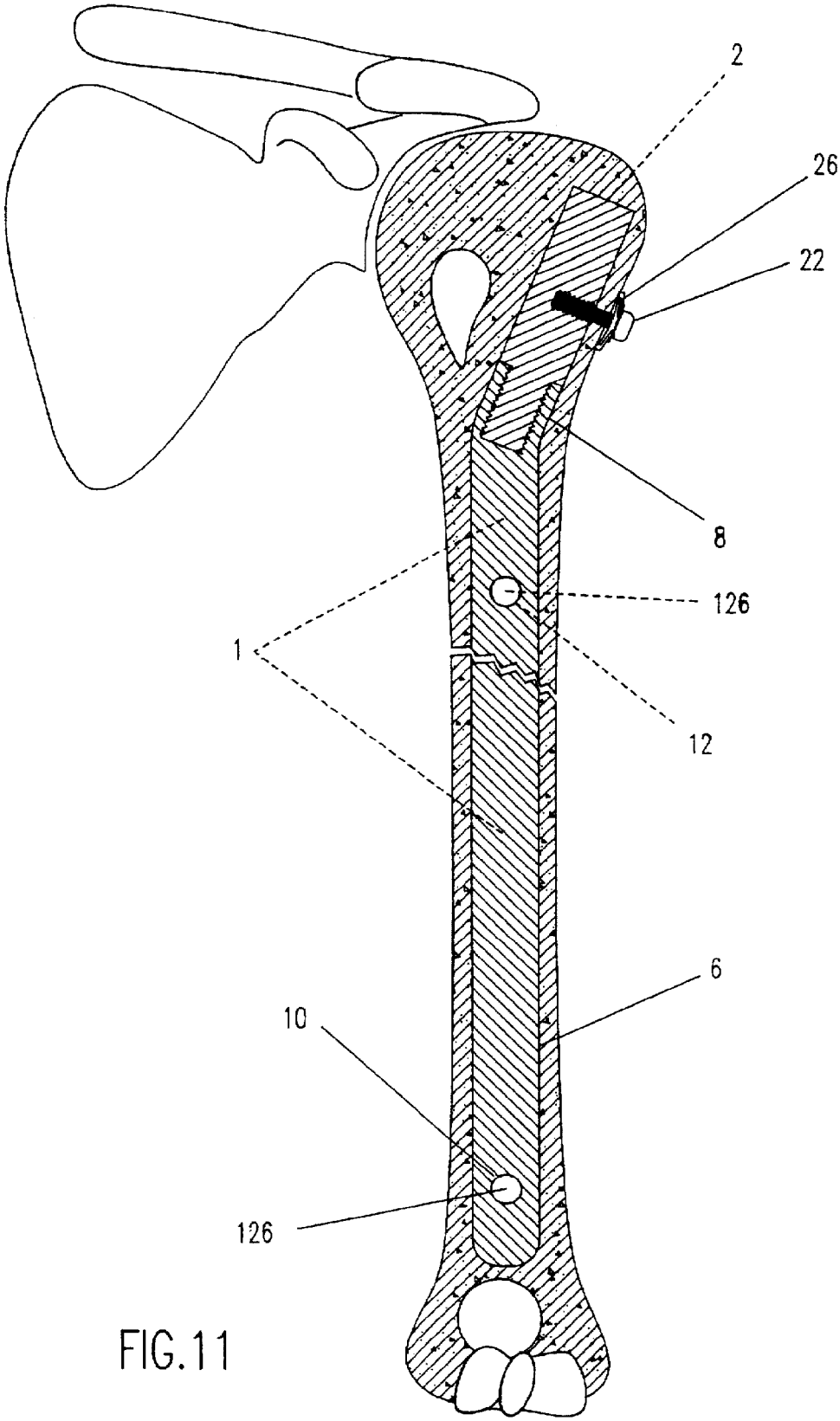
FIG. 11 is a view of the invention applied to a humeral (diaphyseal) shaft fracture.

FIG. 11 displays the invention as applied to a humeral shaft fracture. Intramedullary rod stem member 1 is inserted into the intramedullary canal of the humerus, and extension member 2 connected to proximal end 8 of stem member 1, in the proximal end of the humerus. Interlocking screws 126, or other stable means, are used to secure distal 6 and proximal 8 ends of stem member 1 to the humerus, through passages 10 and 12 respectively. One or more stabilizing screws 22 or 24 may be affixed to provide additional stability with or without claw washer 26.

Figure 12:
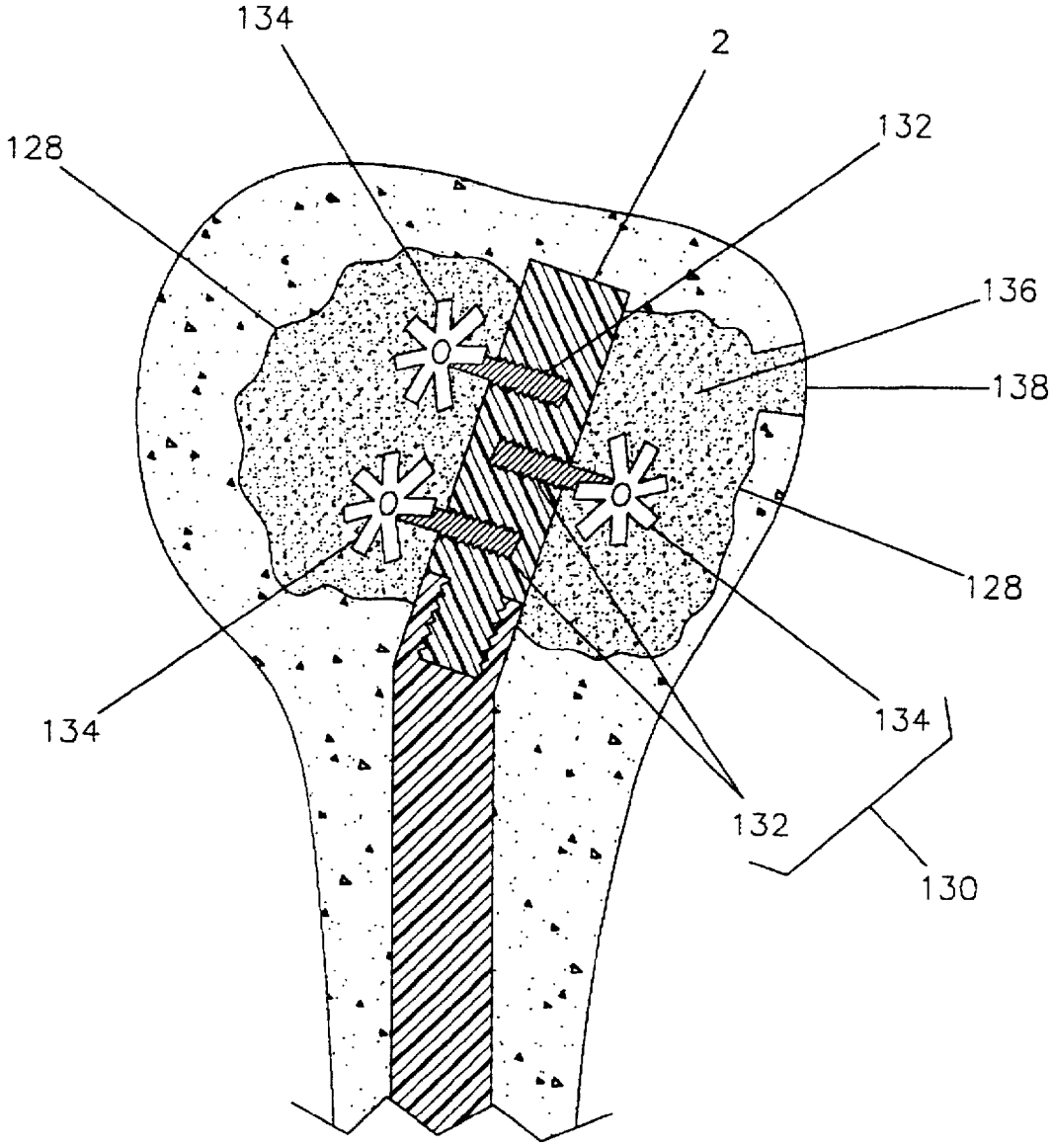
FIG. 12 is a view of the invention applied to a proximal humeral cavity, incorporating anchoring means.
Figure 13:
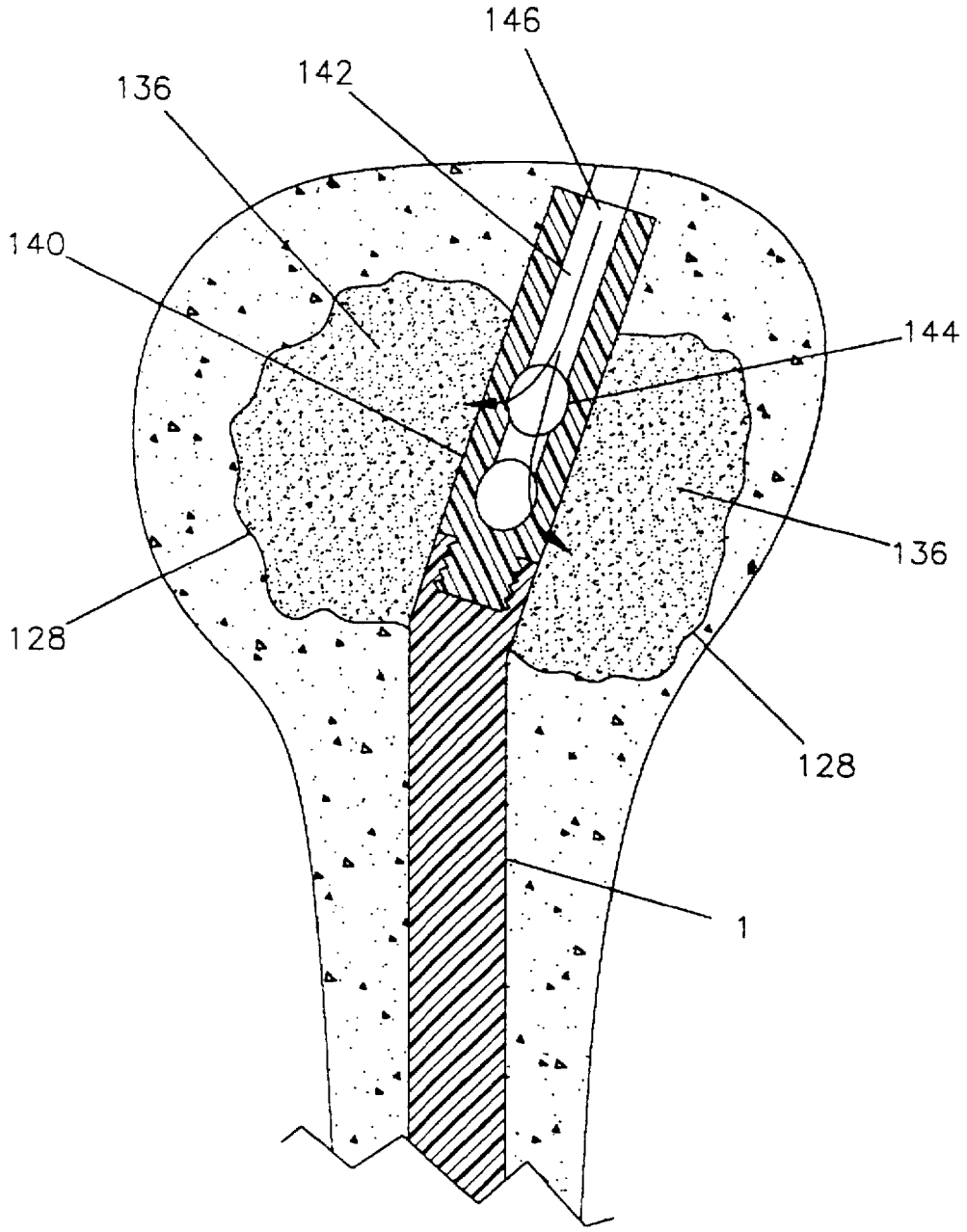
FIG. 13 shows an alternative embodiment of the invention as applied in FIG. 12, but with an extension member that is hollow and slotted for passage of cement.

Another embodiment of the present invention will be described in reference to FIGS. 12 and 13. The objective of this embodiment of the present invention is to treat intraosseous proximal humerus conditions in which a void or cavity is formed in the proximal humerus with or without an associated fracture. FIGS. 12 and 13 display possible applications of the invention to proximal humerus voids or cavities 128. It will be understood by one reasonably skilled in the art that such voids weaken the structural integrity of the bone, possibly resulting in pathologic or impending fractures.

Referring to FIG. 12, it will be seen that before or after extension member 2 is installed in the proximal humerus, one or more anchor devices 130 are attached to extension member 2. Anchor device 130 includes a threaded end 132 for attaching to extension member 2. Anchor device 130 additionally includes an opposite end incorporating one or more flanges 134 extending radially outward from the stem. It will be understood by one skilled in the art that polymethylmethacrylate or some other form of bone cement 136 or substance suitable for both bonding and structural support can then be introduced into void 128 through passageway 138 in the bone. The passageway is created out of the necessity to remove the tumor or substance causing the void prior to the insertion of the cement. The substance 136 introduced, bonding to extension member 2 and anchor device 130, and will securely reconstruct the proximal humerus defect.

Referring to FIG. 13, an alternative method of treating an intraosseous void 128 uses a slotted, hollow extension member 140. The extension member 140 mounts to the stem member 1 shown in FIG. 1 by any of the structures and methods used for mounting the extension member 2 described for the first embodiment. The extension member 140 contains a passage 142 and exit slots 144. After extension member 140 is installed in the proximal portion of the humerus, polymethylmethacrylate or some other form of bone cement or substance suitable for both bonding and structural support is then introduced through proximal end 146 of the passage 142. The substance flows out of the slots 144 in extension member 140 and into the void 128, thereby incorporating the intramedullary rod into the cement construct and adding stability to the reconstructed humerus.

FIGS. 14A and 14B depict a three-part greater tuberosity proximal humeral fracture, and its repair, using the embodiments of FIGS. 1. FIG. 14A is a view of the repaired fracture, showing two installed sets of screws 22 and washers 26, each threaded into the extension member 2. One combination of screw 22 and washer 26, (shown oriented into the page) secures the head and lesser tuberosity fragment 66a (one part)

to the extension member while the other screw 22 and washer 26 (shown lateral to the page) secures the greater tuberosity part 66b to the extension member. The humeral shaft is secured by the screw (not numbered) through the proximal transverse passage 12 in the stem member 1. FIG. 14B is a cut-away view showing the FIG. 1 embodiment in place. Each of the screw 22 and washer 26 combinations are positioned to avoid interference with shoulder motion and to avoid impingement.

Figure 15:
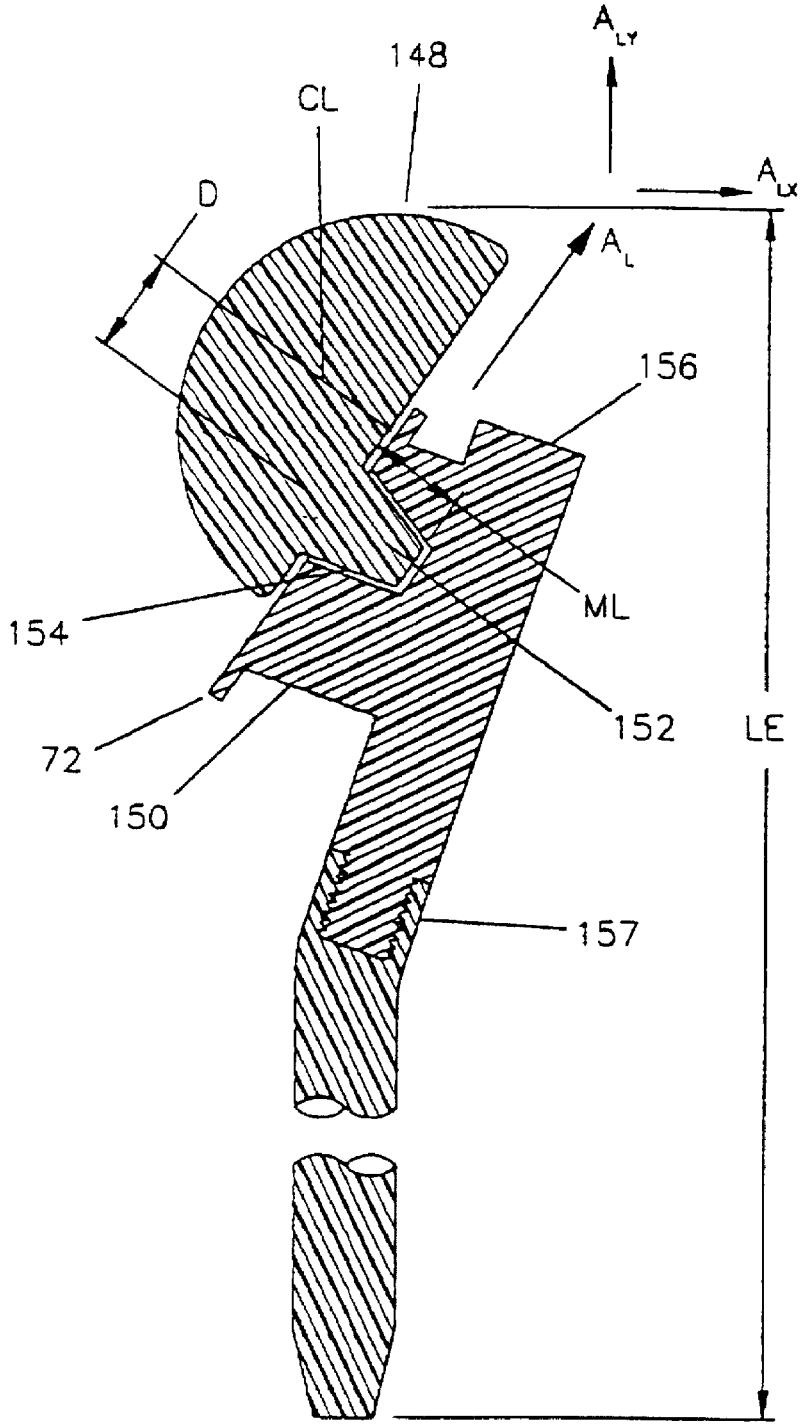
FIG. 15 depicts another embodiment of the present invention, having a prosthetic head attached by Morse taper pin.

Still another embodiment of the present invention is depicted in cross-sectional view in FIG. 15. This embodiment is a variation of the embodiment of FIG. 10 wherein a prosthetic head 148 is attached to an angled fixation bracket 150 by a Morse taper, such as the tapered pin 152 and tapered female end 154, or by an equivalent mechanism. In the depicted example male end 152 is either attached to or unitary with the head 148 and fits into a tapered female end 154 formed in the angled fixation bracket 150. The securing of the male end 152 into the tapered female end 154 is effected by tapping with a mallet. The angled fixation bracket 150 is shown, for the depicted example, as unitary with the extension member 156. Alternatively, the bracket 150 could be mounted by, for example, screws (not shown) to the extension member 156.

The extension member 156 may be formed of a drillable material, such as extension member 2 of the FIG. 1 embodiment, to enable insertion of pressure screws 22 and washers 26. The extension member 156 is shown as connected to stem member 157, which is formed like the stem member 1 of FIG. 1, by a threaded portion (not numbered) of the extension and a corresponding threaded hole (not numbered) in the proximal end of the stem 1. However, as described for the embodiments above, the extension member 156 may be removably connected to stem 157 by other methods, or the members 157 and 156 can be permanently connected, such as by forming the two as a unitary structure.

As shown in FIG. 15, the Morse taper pin 152 is offset by a distance D relative to the centerline CL of the head 148. The amount of offset D controls the distance LE from the upper extremity of the head 148 to the lower extremity of the distal end of stem member 157. The distance LE controls the humeral length upon the stem member 157 being anchored, as described in reference to FIGS. 1 and 11, to the humerus. In other words, offset D displaces the prosthetic head 148 a corresponding distance in the direction of arrow AL, thereby increasing the distance LE and humeral length. Effecting a correct humeral length, i.e., that of the recipient's normal humeral length, is required in order to obtain a correct length-tension curve for the surrounding musculature and to maximize the stability of the prosthetic humeral head in the glenoid fossa that articulates with it. If the length LE, and hence humeral length, is set too short then the surrounding muscles may be too lax to function correctly and the prosthetic head might dislocate from the glenoid.

The humeral length problem can be easily solved with this embodiment. Specifically, by having a set of heads 148 at the time of installation with numerical values of D over a selected range, including a no-offset zero where the pin 152 is on the centerline, adjustment of the length LE can be effected, and hence the correct humeral length established. This addresses a factor in prosthetic replacement of the proximal humerus in that for related fractures, the surgical neck fracture is often lower than the cut made when placing the prosthesis in a nonfractured humerus. The result of the surgical neck fracture being lower than the cut is that when one completely inserts, or "sinks," the prosthesis to the level of the fracture it may be too distal in the humerus, thereby causing the length problem. However, by having a range of heads 148 on hand at the time of installation, with varying offsets D, the method and apparatus of this embodiment solves this length problem.

Further to this embodiment is that the length ML of the Morse pin 152 can be selected to compensate for the component of the offset D that laterally offsets the humeral head. Referring to FIG. 15, the reason is that the D displaces the head 148 in the direction of the arrow AL, offset, i.e., parallel to the plate 72 of FIG. 15. The desired component of AL, the one affecting humeral length, is along the longitudinal axis ALy of the stem member 157, i.e., along the axis of the humeral shaft (not shown) into which the stem 157 is inserted. However, another component of AL is perpendicular to the axis of the stem member 157 (i.e., perpendicular to the axis of the humeral shaft) and is labeled as ALx. If not compensated for, this displacement in the ALx direction would cause a lateral displacement of the humeral head 148. This is solved by forming the length ML of the Morse pin 152 in proportion to the amount of offset D. It is also envisioned that, in addition to having a set of prosthetic heads 148 with varying offsets D, that a set of heads 148 of various spherical diameters (not labeled) could be available at time of installation. This would allow an optimal head diameter that matched the original humeral head and offset D to be chosen, to obtain both a proper humeral length and a functional cooperation of the head 148 to the recipient glenoid fossa.

Optional to the FIG. 15 embodiment is to form the Morse taper pin 152 and hole 154 as a tapered square (not shown) or with splines (not shown), or with a longitudinal slot and key (not shown), or other shapes such as trapezoidal (not shown) to provide resistance to rotation of the head 148 about the longitudinal axis of the pin 152.

Figure 16:
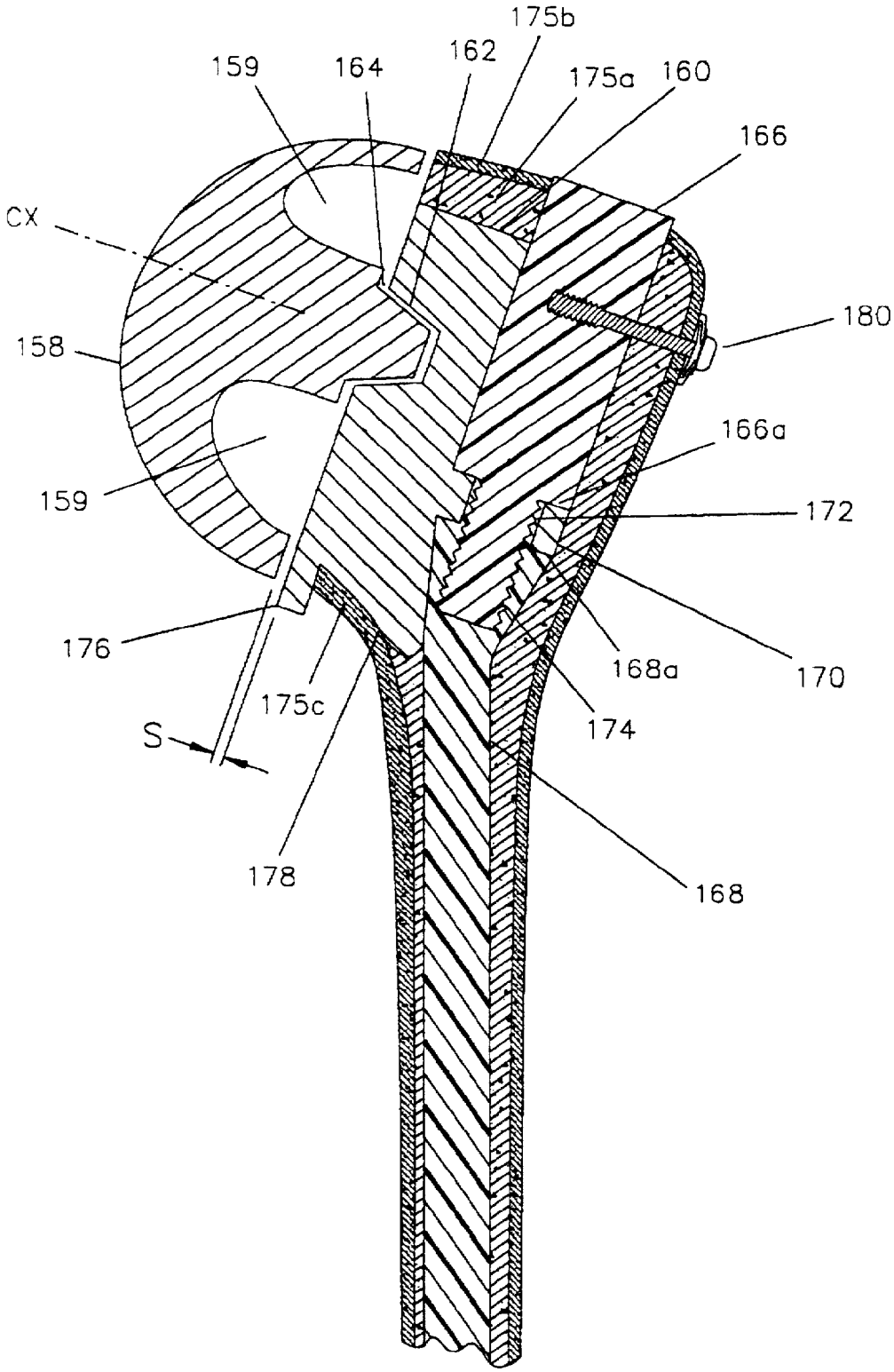
FIG. 16 shows a variation of a prosthetic head of the embodiment of FIG. 15, having an offset Morse attachment and using a spacer bracket.

A variation of the above embodiment is shown in the cross-sectional view of FIG. 16. In this embodiment a prosthetic head 158 is attached to a spacer bracket 160 by a Morse taper structure shown, for this example, as a Morse tapered hole 162 formed on the bracket 160, cooperating with a Morse pin 164 formed on, or attached to, the head 158. The spacer bracket 160 differs from the bracket 150 of the above embodiment in its attachment to the extension member 166 and stem member 168. Specifically, the spacer bracket 160 has a flange 170, shown in cross section in FIG. 16, having a hole 172 through which the threaded portion 174 of extension member 166 passes. When the extension member 166 is tightened by, for example, rotation with pliers (not shown) the flange 170 is compressed between the surface 166a of the extension member 166 and surface 168a of the stem 168. FIG. 16 depicts the embodiment in a healed state and shows, in cross section, a bone portion 175 formed above the bracket 160 and between the extension member 166 and prosthetic head 158. The bone region 175b represents cortical bone and the region 175a represents cancellous bone.

Referring to FIG. 16, the prosthetic head 158 is shown as having a circular cavity or recess 159 for reduced mass. Further, the prosthetic head 158, Morse pin 164 and Morse tapered hole 162 are preferably dimensioned so that when the Morse pin 164 is secured to the hole 162 a space S remains between the head 158 and bracket 160. Also, the example spacer bracket 160, as shown in FIG. 16, includes an optional support collar 176 allowing the spacer bracket to lie securely on the humeral calcar (cortical bone) 175c. The example spacer bracket 160 of FIG. 16 is also shown as having an optional projection 178 to effect a more secure and conforming engagement with the humerus. Further, so as to prevent possible rotation of the spacer bracket 160 about the extension member 166 and stem 168, a groove (not shown) may be formed along a length of the bracket contacting the extension member 166 with a corresponding slot (not shown) formed in the extension member 166.

The prosthetic head 158 and spacer bracket 160 of this embodiment are preferably formed of a chromium-cobalt alloy or similar biocompatible alloy. The extension member 166 may be formed of metal or, as shown in the example of FIG. 16, can be formed of a drillable material as described for extension member 2 of the previous embodiments. Accordingly, as shown in FIG. 16, a compression screw and washer assembly 180, which is identical to the compression screw 24 and washer 26 of the previous embodiments, can be used to secure a portion of the tuberosity to the extension member 166. The stem member 168 is formed with transverse holes (not shown) to enable fixation of the stem to the humerus, as described for the stem member 1 of the previous embodiments. Also, as described for previous embodiments, the proximal end of the stem member could have an externally threaded stud (not shown) fit into a corresponding hole (not shown) in the extension member 166. Alternatively, although not shown, the Morse pin could be formed on the spacer bracket and the hole in the prosthetic head. Further, as described for the embodiment of FIG. 15, the Morse tapered hole 162 can be offset from the centerline CX of the head 158, thus allowing control of the humeral length and head position.

It will now be apparent to those skilled in the art that other embodiments, improvements, details, and uses can be made consistent with the letter and spirit of the foregoing disclosure and within the scope of this patent. For example, the intramedullary rod apparatus in FIG. 1 could be unitary, that is, stem member 1 and extension member 2 could include a one-piece structure formed of plastic or a bioabsorbable material. Thus, the present invention is limited only by the following claims, construed in accordance with the patent law.

What is claimed is:

1. A bone stabilizing device, comprising:

a stem member, extending substantially along a first longitudinal axis, for insertion into a *medullary* bone cavity, said stem member having a distal end and a proximal end;

[an] *a substantially cylindrical* extension member *positioned substantially outside of the medullary bone cavity*, extending substantially along a second longitudinal axis, having a distal and a proximal end, said distal end connected to said proximal end of said stem member; and means for securing a *fractured metaphyseal or epiphyseal* bone to said extension member comprising a securing member having a first end [affixed into] *mechanically attached to* the extension member and a second end spaced apart from said extension member, and means connected to said second end for pressing on a *cortical* surface of the bone to urge the bone against said extension member*, wherein a third longitudinal axis of the securing member is unaligned with the second longitudinal axis of the extension member*.

2. A bone stabilizing device according to claim 1 wherein said extension member consisting essentially of a plastic material substantially devoid of a metal casing, and said [means for securing bone] *plastic* material further includes a threaded hole transversely disposed in and opening out of said extension member, and said securing member includes an attachment screw having a threaded portion at its first end engaged with said threaded hole and having a screw head at its second end spaced apart from said extension member, wherein a rotation of said threaded attachment screw urges said screw head against the bone material and thereby urges the bone material against the extension member.

3. A bone stabilizing device according to claim 2, further comprising a washer disposed between said screw head and an outer surface of said extension member, wherein a rotation of said threaded attachment screw urges said washer against the bone material and thereby urges the bone against the extension member.

[4. A bone stabilizing device according to claim 1, further comprising a positioning means for connecting a bone to said extension member at a predetermined angle.]

[5. A bone stabilising device according to claim 4, wherein said positioning means comprises an angled fixation bracket connected to said extension member, said angled fixation bracket having a support plate for supporting the bone having a plurality of passages formed therethrough; and a means for connecting the bone to the support plate through said plurality of passages.]

[6. A bone stabilizing device according to claim 4, wherein said positioning means comprises an angled fixation bracket connected to said extension member, said angled fixation bracket having a support plate for supporting the bone and further comprising a plurality of mounting screws, said screws each having a first and second threaded portion, said first portion having a first thread pitch and said second portion having a second thread pitch greater than said first pitch, said screws being arranged such that said first portion is threaded into said bone and said second portion is threaded into said support plate, whereby a rotation of said mounting screws urges said bone against said support plate.]

[7. A bone stabilizing device according to claim 4, wherein said positioning means comprises:

an angled fixation bracket connected to said extension member, said angled fixation bracket having a support plate for supporting the bone;

a plurality of cannulated mounting screws each having a head on a first side of said support plate and a threaded portion extending into a bone on a second side of said support plate, said cannulated screws each having a through-bore; and a suture thread passing through the through-bore of at least two of said cannulated screws and through said bone.]

[8. A bone stabilizing device according to claim 7 wherein at least one of said cannulated screws includes a suture tie bar located proximal to the head thereof.]

[9. A bone stabilizing device according to claim 4 wherein said positioning means comprises a plurality of rods, each of said rods having:

a first portion extending through a corresponding lateral clearance hole in said extension member;

a threaded portion for threaded engagement into said bone;

means for moving said rod axially through said lateral clearance hole; and means for locking said rod to said extension member at a selectable axial position within said clearance hole.]

10. A bone stabilizing device according to claim 1, further comprising:

a prosthetic humeral head;

positioning means for connecting said prosthetic humeral head to said extension member in a predetermined position humeral neck-shaft angle; and means for locking prosthetic humeral head in said position.

11. A bone stabilizing device according to claim 10, wherein said positioning means are removably connected to at least one of said prosthetic humeral head and said extension member.

12. A bone stabilizing device comprising:

a stem member, extending substantially along a first longitudinal axis, for insertion into a bone cavity;

[an] *a substantially cylindrical* extension member, connected to said stem member, *said extension member* having a plastic material[.] *and* extending substantially along a second longitudinal axis;

a prosthetic head having a mounting surface and a hemispherical shaped surface formed about a centerline; and means for securing said prosthetic head to said extension member, said means comprising:

a support member connected to said extension member having a head support surface facing toward said mounting surface of said prosthetic head, said head support surface forming a predetermined angle with said extension member, a hole formed in said support member and projecting into said head support surface toward said extension member, and a pin connected to said mounting surface of said prosthetic head; and means for securing a *fractured metaphyseal* bone to said extension member, said means for securing bone comprising:

an attachment screw having a threaded portion engaged with said extension member and having a screw head spaced apart from an outer surface of said extension member, wherein a rotation of said threaded attachment screw urges said screw head against the bone and thereby urges the bone against the extension member.

13. A bone stabilizing device comprising:

a stem member, extending substantially along a first longitudinal axis, for insertion into a bone cavity, said stem member having a distal end and a proximal end;

an extension member, extending substantially along a second longitudinal axis, having a distal and a proximal end;

a spacer bracket having a mounting flange with a hole formed therein and having a support face;

a threaded extension, formed on one of said proximal end of said stem member and said distal end of said extension member, said threaded extension passing through said hole in said mounting flange and threading into a threaded hole formed in the other of said proximal end of said stem member and said distal end of said extension member, so as to securely mount said mounting flange to said extension member and said stem member;

a prosthetic head having a substantially planar surface and having a hemispherical shaped surface formed about a centerline extending normal to said planar surface; and means for securing said prosthetic head to said spacer bracket, said means comprising a tapered hole extending normal into a plane of the support face of said spacer bracket and a tapered pin connected to the planar surface of said prosthetic head.

14. A bone stabilizing device according to claim 13, wherein said extension member includes a plastic material, and further comprising:

means for securing a bone to said extension member, said means for securing said bone comprising:

a screw having a threaded portion engaged with said extension member and having a screw head spaced apart from an outer surface of said extension member, and a washer disposed between said screw head and an outer surface of said extension member, wherein a rotation of said threaded screw urges said washer against the bone and thereby urges the bone against the extension member.

*15. A bone stabilizing device according to claim 1, wherein the securing member comprises a screw.*

*16. A bone stabilizing device according to claim 15, wherein the screw comprises a pressure type stabilizing screw, a suture type stabilizing screw, or an anchor with a threaded end and at least one flange at the second end.*

*17. A bone stabilizing device according to claim 15, wherein the means connected to said second end for pressing on a cortical surface of the bone comprises a head of said screw.*

*18. A bone stabilizing device according to claim 17, wherein said second end further comprises a washer.*

*19. A bone stabilizing device according to claim 18, wherein said washer comprises a claw washer.*

*20. A bone stabilizing device according to claim 19, wherein said claw washer comprises a slot.*

*21. A bone stabilizing device according to claim 1, wherein a distal tip of said first end of the securing member protrudes from the extension member.*

*22. A bone stabilizing device according to claim 1, wherein the first longitudinal axis forms an angle with the second longitudinal axis.*

*23. A bone stabilizing device according to claim 22, wherein the angle is less than 180 degrees.*

*24. A bone stabilizing device according to claim 1, wherein the securing member comprises at least one screw wherein the first end of the at least one screw is a threaded end, and wherein said means connected to said second end for pressing on a cortical surface of the bone to urge the bone against said extension member comprises at least one flange at the second end; and*

*wherein the bone stabilizing device further comprises a second means for securing the bone to said extension member.*

*25. A bone stabilizing device according to claim 1, wherein said bone is separated from an adjacent bone by a fracture line and said securing member crosses the fracture line to secure said bone to said extension member.*

*26. A bone stabilizing device according to claim 1, wherein said means for securing a bone to said extension member comprising more than one securing member.*

* * * * *